United States Patent [19]
Yomtov et al.

[11] Patent Number: 5,388,578
[45] Date of Patent: Feb. 14, 1995

[54] IMPROVED ELECTRODE SYSTEM FOR USE WITH AN IMPLANTABLE CARDIAC PATIENT MONITOR

[75] Inventors: Barry M. Yomtov; Paul E. Kreyenhagen, both of Bellevue, Wash.

[73] Assignee: InControl, Inc., Redmond, Wash.

[21] Appl. No.: 43,269

[22] Filed: Apr. 6, 1993

Related U.S. Application Data

[62] Division of Ser. No. 820,580, Jan. 14, 1992, Pat. No. 5,313,953.

[51] Int. Cl.⁶ ............................................. A61B 5/042
[52] U.S. Cl. ............................................. 128/642; 607/37
[58] Field of Search ................. /37, 36, 119, 122, 129, /130, 9, 116, 123, 132, 27, 9; 128/642, 696, 899

[56] References Cited

U.S. PATENT DOCUMENTS

| | | | |
|---|---|---|---|
| 3,253,595 | 5/1966 | Murphy, Jr. et al. | 607/129 |
| 4,289,138 | 9/1981 | Halvorsen | 128/642 |
| 4,387,717 | 6/1983 | Brownlee et al. | 607/27 |
| 4,424,818 | 1/1984 | Doring et al. | 607/130 |
| 4,579,119 | 4/1986 | Callaghan | 607/13 |
| 4,595,012 | 6/1986 | Webler et al. | 128/642 |
| 4,892,102 | 1/1990 | Astrinsky | 607/27 |
| 4,895,152 | 1/1990 | Callaghan et al. | 607/13 |
| 4,995,389 | 2/1991 | Harris | 607/37 |
| 5,087,243 | 2/1992 | Avitall | 607/129 |
| 5,105,826 | 4/1992 | Smits et al. | 128/642 |
| 5,133,422 | 7/1992 | Coury et al. | 607/123 |
| 5,158,097 | 10/1992 | Christlieb | 128/642 |
| 5,172,694 | 12/1992 | Flammang et al. | 128/696 |
| 5,203,348 | 4/1993 | Dahl et al. | 128/642 |

FOREIGN PATENT DOCUMENTS

| | | | |
|---|---|---|---|
| 0148300 | 5/1981 | Germany | 607/37 |
| 0149310 | 7/1981 | Germany | 607/37 |
| 2127629 | 4/1984 | United Kingdom | 607/37 |

*Primary Examiner*—William E. Ramm
*Assistant Examiner*—Kennedy J. Schaetzle
*Attorney, Agent, or Firm*—Richard O. Gray, Jr.

[57] ABSTRACT

An implantable cardiac monitor is arranged for detecting both arrhythmias and ischemia of the human heart. The monitor includes subcutaneous electrodes for establishing electrical contact with the heart and a sense amplifier coupled to each electrode for generating an electrocardiogram of a heart beat sensed at each of the electrodes. The electrocardiograms are digitized and the digital samples thereof are stored in a memory. A microprocessor processes the digital samples of the electrocardiograms and generates characterizing data indicative of the physiology of the heart. The cardiac monitor includes telemetry to permit the cardiac data to be interrogated externally of the patient for obtaining the generated cardiac data indicative of arrhythmic and ischemic episodes.

1 Claim, 24 Drawing Sheets

IMPROVED ELECTRODE SYSTEM FOR USE WITH AN IMPLANTABLE CARDIAC PATIENT MONITOR

This is a division of application Ser. No. 07/820,580, filed Jan 14, 1992, now U.S. Pat. No. 5,313,953.

BACKGROUND OF THE INVENTION

The present invention generally relates to a cardiac monitor. The present invention more particularly relates to a fully implantable cardiac monitor for monitoring the physiology of the heart and which is externally programmable for detecting either arrhythmias of the heart or ischemia or both. The implantable cardiac monitor generates data indicative of these conditions and stores the data in memory for later retrieval externally of the patient through telemetry. The present invention is further directed to electrode systems for use with the implantable cardiac monitor for sensing heart activity.

Coronary artery circulation normally supplies sufficient blood flow to the heart to meet the demands of the heart muscle (myocardium) as it labors under a widely varying workload. An imbalance that arises between this supply and demand usually precipitates angina pectoris (pain). When the imbalance becomes excessive, myocardial infarction results. Myocardial infarction is necrosis or death of cardiac tissue resulting from the lack of blood flow to the heart. For example, the narrowing of a major coronary artery by more than fifty percent (50%) impairs nutrient blood flow under conditions of myocardial demand.

By far the most common underlying pathologic process that gives rise to the narrowing of a major coronary artery is atherosclerosis. In most patients suffering from atherosclerosis, plaque develops in the proximal segments of the coronary arteries. In other patients, this condition may be diffuse and may occur in both proximal and distal vessels.

Increases in oxygen consumption cause ischemia if coronary artery blood flow cannot rise to meet a higher demand. The clinical manifestations of ischemia are angina, myocardial infarction, congestive heart failure, and electrical instability (arrhythmia). The last mentioned symptom is assumed to account for most of the sudden cardiac death syndrome patients.

Silent ischemia (ischemia without angina) is common and may result in a myocardial infarction without warning. It has been reported that twenty-five percent (25%) of patients hospitalized with a myocardial infarction have no pain and over fifty percent (50%) of ischemic episodes occur without associated pain.

In treating ischemia, the primary goal of medical therapy is to reduce oxygen consumption and increase blood supply by reducing vascular tone (improving collateral flow) preventing thrombosis and opening or bypassing the blockage in the artery or arteries affected. If a clot is causing the blockage, a thrombolytic drug may be used to open the occluded artery. The most direct way to increase blood supply is to revascularize by coronary artery bypass surgery or angioplasty.

Cardiac electrical instability (arrhythmia) may occur during ischemic events and is also a common condition after a myocardial infarction. Since cardiac arrhythmias such as ventricular tachycardia can degenerate into ventricular fibrillation which is life threatening, these arrhythmias are of great concern to the physician or cardiologist. To control such arrhythmias, the cardiologist may choose to treat the patient with antiarrhythmic drugs.

The testing of the effectiveness of such drugs in reducing the number and severity of arrhythmias is very difficult. This is due to the fact that arrhythmias occur at any and all times. In attempting to test the effectiveness of such drugs, patients are often required to wear an external monitor for periods of twenty-four (24) or forty-eight (48) hours that record all cardiac signals during these periods. Also, the physician may submit a patient to extensive electrophysiologic testing which is often performed in a hospital. The physician then uses the results of such testing to assist in determining the course of such drug therapy.

Myocardial infarctions often leave patients with a permanent arrhythmogenic condition even after coronary artery bypass surgery or angioplasty. Such patients are in need of close monitoring for both arrhythmic events as well as further deterioration of the patency of the cardiac vessels.

After revascularization to increase blood supply to the myocardium, the cardiologist must continually submit such patients to diagnostic tests to determine if the revascularization procedure has remained effective. In angioplasty patients, studies have indicated that twenty-five percent (25%) of those patients will experience restenosis within a period of six (6) months. In those patients having coronary artery bypass surgery, restenosis may occur anywhere from a few hours to several years from the time of such surgery. Studies have indicated that after approximately five (5) years, patients having coronary artery bypass surgery should be monitored closely.

To diagnose and measure ischemic events suffered by a patient, the cardiologist has several tools from which to choose. Such tools include twelve-lead electrocardiograms, exercise stress electrocardiograms, Holter monitoring, radioisotope imaging, coronary angiography, myocardial biopsy, and blood serum enzyme tests. Of these, the twelve-lead electrocardiogram (ECG) is generally the first procedure to be utilized to detect a myocardial infarction. An exercise stress electrocardiogram is generally the first test to be utilized for detecting ischemia since resting twelve-lead electrocardiograms often miss the symptoms of ischemia. Unfortunately, none of the foregoing procedures provide an ongoing and continuous evaluation of a patient's condition and are therefore only partially successful at providing the cardiologist with the information that the cardiologist requires in determining the proper corrective course of action.

There is therefore a need in the art for an implantable cardiac patient monitor capable of providing twenty-four (24) hour a day monitoring of patients for either the sudden onset of restenosis or a new occlusion or a serious arrhythmic event. The present invention provides such an implantable cardiac patient monitor. By virtue of the present invention, long-term trends in ischemia, heart rates and arrhythmias may be monitored and recorded. Also, by virtue of the present invention, high-risk patients can be instructed to seek aid immediately to avoid permanent cardiac tissue damage due to a thrombus. In addition, by virtue of the present invention, the cardiologist can use the ischemia trend data to guide further therapy to match changing conditions of a patient whether the patient is improving or deteriorating.

Arrhythmias common to myocardial infarction patients may also be monitored and these conditions may also be trended as well. Such information can be especially useful to the cardiologist in adjusting antiarrhythmic drug therapy to maximize such therapy and minimize side effects. Hence, the implantable cardiac patient monitor of the present invention is capable of providing the cardiologist with ischemic and heart rhythm information not previously available in the prior art which will enable a physician to eliminate or delay certain diagnostic tests and enable the physician to maximize drug therapy.

SUMMARY OF THE INVENTION

The present invention provides a cardiac monitor for monitoring the physiology of a human heart. The monitor is fully implantable beneath the skin of a patient and includes electrode means for establishing electrical contact with the heart, sensing means coupled to the electrode means for generating an electrocardiogram of each heart beat of the heart and processing means responsive to the electrocardiograms corresponding to natural heart beats for detecting arrhythmias of the heart and generating arrhythmia data characterizing the arrhythmias. The cardiac monitor further includes memory means coupled to the processing means for storing the arrhythmia data and telemetry means for transmitting the arrhythmia data to a nonimplanted external receiver.

The processing means is further responsive to the electrocardiograms for detecting ischemia of the heart and is programmable by an external programmer for detecting arrhythmias of the heart, for ischemia of the heart, or for detecting both arrhythmias and ischemia of the heart.

The present invention further provides a cardiac monitor for monitoring the physiology of a human heart wherein the monitor is fully implantable beneath the skin of a patient. The cardiac monitor includes electrode means for establishing electrical contact with the heart, sensing means coupled to the electrode means for generating an electrocardiogram of each heart beat of the heart and data generating means coupled to the sensing means for generating electrocardiogram data for each generated electrocardiogram. The cardiac monitor further includes processing means responsive to the electrocardiograms corresponding to natural heart beats for processing the electrocardiogram data to generate characterizing data indicative of the physiology of the heart and memory means coupled to the data generating means and to the processing means for storing the electrocardiogram data and the characterizing data. The processing means obtains the electrocardiogram data from the memory means and processes the electrocardiogram data at times in between the heart beats.

The present invention further provides a cardiac monitor for monitoring the physiology of a human heart wherein the monitor is fully implantable beneath the skin of a patient and includes electrode means including first and second electrodes for establishing electrical contact with the heart to detect heart beats of the heart, sensing means coupled to the first and second electrodes for generating first and second respective electrocardiograms of each heart beat of the heart and processing means responsive to the first and second electrocardiograms for detecting arrhythmias of the heart and generating arrhythmia data characterizing the arrhythmias. The cardiac monitor further includes memory means coupled to the processing means for storing the arrhythmia data and telemetry means for transmitting the arrhythmia data to a nonimplanted external receiver.

The present invention still further provides an electrode system for use with a fully implantable cardiac monitor of the type including electrical circuitry for monitoring the physiology of the human heart and having an enclosure for containing the electrical circuitry wherein the enclosure includes an upper perimeter. The electrode system includes an electrically insulating header assembly sealingly engaged with the upper perimeter of the enclosure, first and second flexible insulative conduits extending from the header, and first and second electrode means carried by each of the first and second conduits respectively. The first and second electrode means each include at least one electrically conductive electrode. The electrode system further includes conductor means extending through the first and second conduits and into the header for coupling the electrodes of the first and second electrode means to the electrical circuitry of the monitor. The conduits and the electrode means are implantable beneath the skin of a patient to dispose the electrodes in non-touching proximity to the heart for establishing electrical contact between the electrodes and the heart.

The present invention still further provides a cardiac monitor for monitoring the physiology of the human heart wherein the monitor is fully implantable beneath the skin of a patient. The cardiac monitor includes a hermetically sealed enclosure defining a cavity having an opened perimeter, and a header sealingly engaging the opened perimeter. The cardiac monitor further includes first and second electrical conductors covering first and second discrete portions of the enclosure for forming first and second sensing electrodes respectively for sensing activity of the heart, a third electrical conductor covering a third discrete portion of the enclosure for forming a reference electrode and circuit means within the enclosure and coupled to the electrodes for monitoring the activity of the heart sensed by the sensing electrodes.

The present invention further provides a cardiac monitor for monitoring the physiology of the human heart wherein the monitor is fully implantable beneath the skin of a patient and includes a hermetically sealed enclosure including a bottom perimeter, and an electrically insulating header sealingly engaging the bottom perimeter, at least one electrode for sensing activity of the heart, circuit means within the enclosure and coupled to the at least one electrode for monitoring the activity of the heart sensed by the at least one electrode and for generating data indicative of the monitored activity of the heart and telemetry means disposed within the header for transmitting the data to a nonimplanted external receiver.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings, in the several figures of which like reference numerals identify identical elements, and wherein:

DETAILED DESCRIPTION

Figure 1:
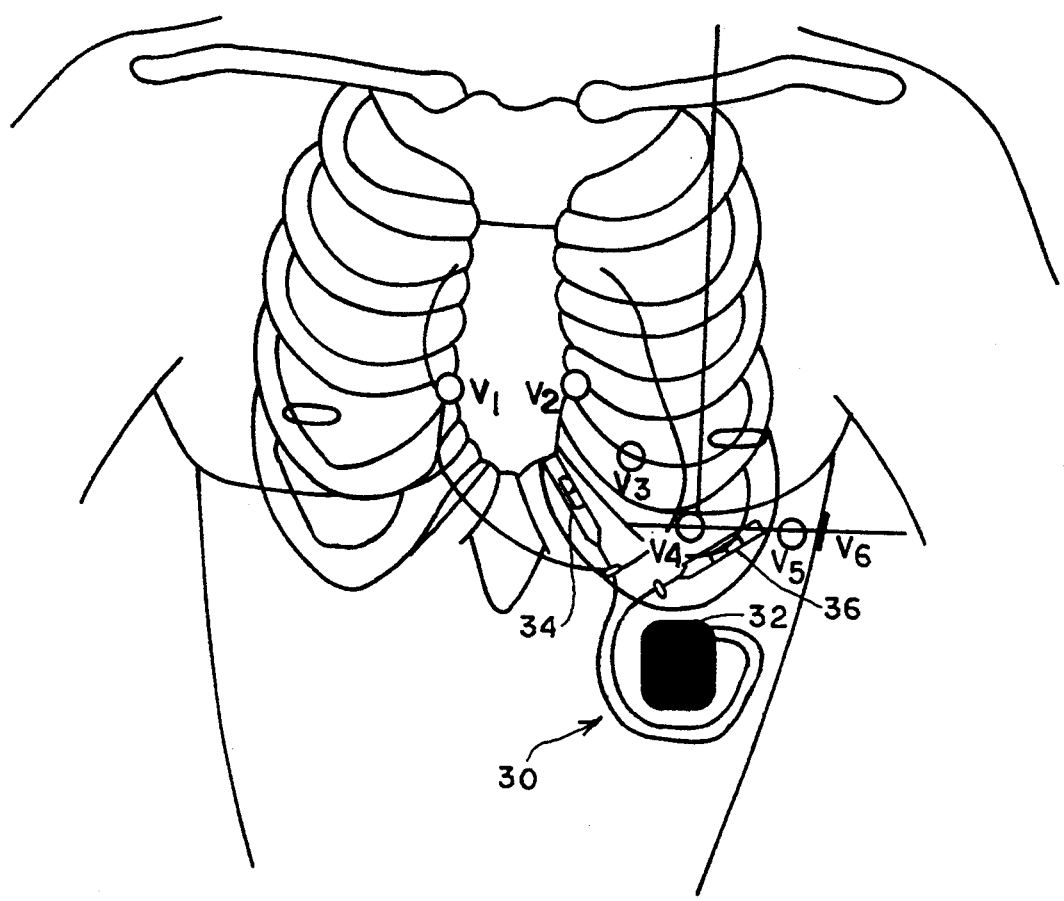
FIG. 1 is a schematic front plan view of the human abdomen and chest illustrating a preferred implantation site of an implantable cardiac monitor embodying the present invention.

Referring now to FIG. 1, it is a schematic front plan view of the human abdomen and chest illustrating a preferred implantation site of an implantable cardiac monitor 30 embodying the present invention. The implantable cardiac monitor 30 generally includes an enclosure 32 and first and second electrode means 34 and 36. The enclosure 32, as will be described hereinafter, includes electronic circuitry for monitoring heart activity and generating data indicative of the physiology of the heart. The electrode means 34 and 36 are coupled to the electronic circuitry within the enclosure 32 by conductor means extending through conduit means in a manner to also be described in greater detail hereinafter.

The enclosure 32 is preferably implanted beneath the skin in the left abdominal area below the diaphragm in the rib cage. The electrode means 34 and 36 preferably comprise subcutaneous electrodes which are also implanted beneath the skin for establishing electrical contact with the heart in non-touching relation thereto. Illustrated in FIG. 1 are six standard locations for external exploring electrodes used for routine clinical electrocardiography designated $V_1$ through $V_6$. The electrode means 34 and 36, as illustrated, are implanted in the precordial area in close proximity to the $V_2$ through $V_6$ locations. As will be seen hereinafter, each of the electrode means 34 and 36 may comprise strip electrodes including one or more discrete conductive electrodes or catheter electrodes including one or more conductive ring-shaped electrodes.

Figure 2:
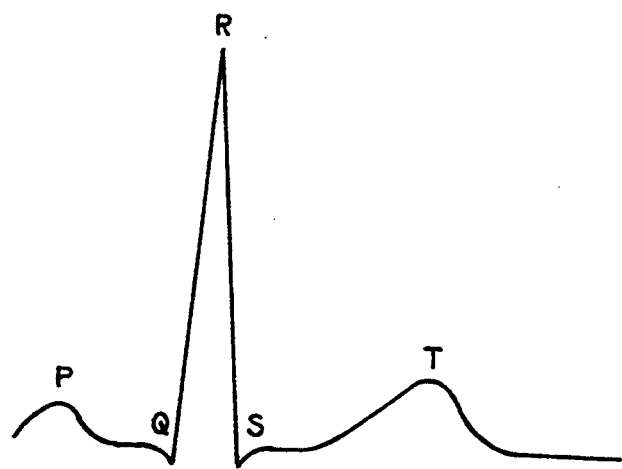
FIG. 2 is a graphic representation of a typical or normal ECG waveform showing the conventional nomenclature for the various portions thereof.

Referring now to FIG. 2, it provides a graphic representation of a typical or normal electrocardiogram (ECG) waveform showing the conventional nomenclature for the various portions thereof. The beginning of a heart beat is initiated by a P wave which is normally a small positive wave. Following the P wave there is an ECG waveform portion which is substantially constant in amplitude. This substantially constant portion will have a time duration on the order of, for example, 120 milliseconds and may be utilized for establishing a baseline for detecting ischemia.

The QRS complex of the ECG then normally occurs after the substantially constant portion with a Q wave which is normally a small negative deflection which is then immediately succeeded by the R wave which is a rapid positive deflection. The R wave generally has an amplitude greater than any other waves of the ECG signal and will have a spiked shape of relatively short duration with a sharp rise, a peak amplitude, and a sharp decline. The R wave may have a duration on the order of 40 milliseconds. However, as described hereinafter, the cardiac monitor 30 distinguishes between normal heart beats of the type illustrated in FIG. 1, for example, and abnormal heart beats which are referred to herein as ventricular beats which are ectopic beats originating in a ventricle of the heart and which is generally characterized by an R wave having a duration which is greater than the duration of the normal R wave morphology of the patient being monitored.

Following the R wave, the QRS complex is completed with an S wave. The S wave may be generally characterized by a small positive inflection in the ECG signal.

Following the S wave is the T wave which is separated from the S wave by the ST segment. The amplitude of the ST segment, in a healthy heart, is generally approximately equal to the baseline following the P wave and preceding the Q wave. As will be seen hereinafter, the cardiac monitor 30 detects ischemia when the amplitude of the ST segment deviates from the baseline following the P wave by an amount greater than a predetermined amount. The T wave is relatively long in duration of, for example, on the order of 150 milliseconds. Following the T wave, which concludes the heart beat, is a substantially constant amplitude until the next P wave occurs.

As will be seen hereinafter, each electrode of the cardiac monitor 30 is coupled to a respective input amplifier. Each input amplifier generates an ECG signal for each heart beat which is digitized by an analog to digital converter and stored in a memory through a direct memory access. Following each heart beat, a microprocessor of the cardiac monitor processes the stored data and generates data indicative of the physiology of the heart being monitored. The microprocessor processes the data and generates the characterizing data after the digital samples of the ECG signals are stored for each heart beat during the time following the T wave of one heart beat and before the P wave of the next heart beat, In processing the stored data, the microprocessor distinguishes between normal heart beats (normal sinus heart beats) and abnormal heart beats (ventricular beats) and logs in memory critical events after beat classification and classifies heart beat rhythms in a manner to be fully described hereinafter.

Figure 3:
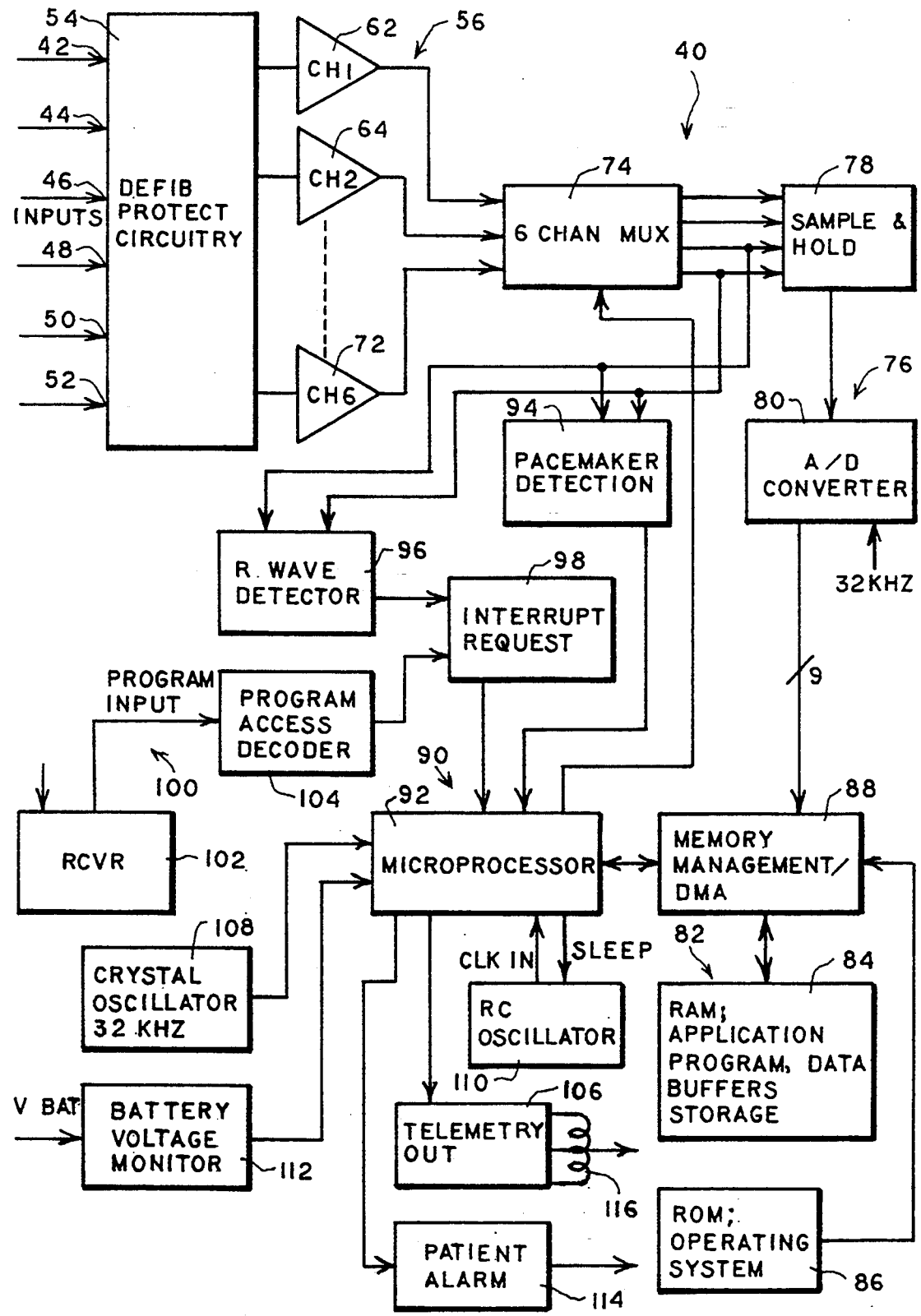
FIG. 3 is a detailed schematic block diagram of the internal circuitry of an implantable cardiac monitor embodying the present invention.

Referring now to FIG. 3, it illustrates in schematic block diagram form, the internal circuitry of the implantable cardiac monitor 30 of FIG. 1 which is contained within the enclosure 32. The cardiac monitor circuitry 40 generally includes a plurality of inputs 42, 44, 46, 48, 50, and 52 which are arranged to be coupled to the electrodes of the electrode means 34 and 36 illustrated in FIG. 1. As will be noted, six such inputs are provided for accommodating electrode means having a total of up to six electrodes. As will be seen hereinafter, in accordance with this preferred embodiment, up to four of the heart activity signals received at inputs 42, 44, 46, 48, 50, and 52 may be utilized for monitoring the physiology of the heart. The particular inputs to be utilized in monitoring the physiology of the heart are externally programmable to allow the cardiologist flexibility in selecting those inputs which provide the best heart activity signals.

The circuitry 40 further includes defibrillation protection circuitry 54, a sensing means 56 comprising a plurality of input amplifiers with each input amplifier corresponding to a respective given one of the inputs. To that end, input amplifier 62 corresponds to input 42, input amplifier 64 corresponds to input 44, and input amplifier 72 corresponds to input 52. The input amplifiers corresponding to inputs 46, 48, and 50 are not illustrated so as to not unduly complicate the figure.

The circuitry 40 further generally includes a multiplexer 74, a data generating means 76 including a sample and hold 78 and an analog to digital converter 80, a memory means 82 including a random access memory 84 and a read only memory 86, and a direct memory access 88. The circuitry 40 further includes a processing means 90 including a microprocessor 92, a pacemaker detector 94, an R wave detector 96, and an interrupt request 98. The circuitry 40 still further generally includes a telemetry input means 100 including a receiver 102 and a program access decoder 104, a telemetry output 106, a crystal oscillator 108, and an RC oscillator 110. Lastly, the circuitry generally includes a battery monitor 112 and a patient alarm 114.

The defibrillation protection circuitry 54 protects the circuitry 40 from defibrillating energy which may be applied to the heart by a ventricular defibrillator. Such circuitry may include zener diodes in a manner well known in the art.

The inputs 42, 44, 46, 48, 50, and 52 are coupled to the inputs of the input amplifiers 62, 64, and 72 through the defibrillation protection circuitry 54. Each of the input amplifiers generates an electrocardiogram representing the heart beats of the heart detected by its corresponding electrode. The outputs of the input amplifiers 62, 64, and 72 are coupled to the multiplexer 74 which, responsive to external programming, selects up to four outputs of the input amplifiers to be utilized for monitoring the physiology of the heart. As a result, the output of the multiplexer 74 includes four channels which are coupled to the sample and hold 78. As illustrated in the Figure, the electrocardiograms provided by the first and second channels of the multiplexer are used for detecting R waves and are thus coupled to the R wave detector 96. In addition, the first and second channels of the multiplexer 74 are also coupled to the pacemaker detector 94 for detecting stimuli applied to the heart by a pacemaker. Such pacemaker detection is provided so that only those electrocardiograms corresponding to spontaneous or natural heart beats of the heart are utilized by the processing means 90 for processing the electrocardiogram data and generating data characterizing the physiology of the heart. To that end, the pacemaker detector 94 is coupled to the microprocessor 92 to cause the microprocessor to disregard electrocardiograms which correspond to heart activity resulting from a pacemaker stimulus.

The first and second channels of multiplexer 74 along with the third and fourth channels of multiplexer 74 are coupled to the sample and hold 78. The sample and hold 78 is coupled to the analog to digital converter 80 which converts the analog electrocardiogram signals being held by the sample and hold 78 to digital samples one at a time in succession. To that end, the analog to digital converter 80 is coupled to the crystal oscillator 108 which provides clocking signals at a rate of, for example, 32 kilohertz. The crystal oscillator 108 continuously provides the clocking signals so that the sample and hold 78 and analog to digital converter 80 continuously generate digitized electrocardiogram data. The digital samples provided by the analog to digital converter 80 are preferably multiple-bit digital samples containing, for example, nine bits. The digital samples of the electrocardiograms are provided to the direct memory access 80 which continuously stores the electrocardiogram digital samples in the random access memory 84.

In addition to storing the digital samples of the electrocardiograms of each of the four utilized channels, the random access memory 84 also stores operating instructions for microprocessor 92 which define the executions to be performed by the microprocessor 92 for processing the electrocardiogram digital samples for in turn generating characterizing data of the physiology of the heart. As will be seen hereinafter, the microprocessor 92 responsive to the operating instructions provided by random access memory 84 and the electrocardiogram digital samples is arranged for monitoring arrhythmias of the heart, ischemia, or both arrhythmias and ischemia depending upon the manner in which the cardiac monitor is externally programmed. As will be seen in FIG. 3A, the random access memory 84 also includes storage locations which are utilized for buffering data to temporarily store such data and storage locations for storing data generated by the microprocessor 92 which is to be more permanently stored and made available to the cardiologist upon external interrogation for the transmission of such data by the telemetry output 106 to an external receiver.

The read only memory 86, in a manner well known in the microprocessor art, stores basic operating system instructions for the microprocessor 92. Such basic system operating instructions may include instructions which permit the microprocessor 92 to perform the input programming and the output telemetry functions for transmitting data to and from an external receiver, to permit the microprocessor to perform reset executions, and to permit the microprocessor to perform self-check operations, for example.

As previously mentioned, the microprocessor 92 processes the stored electrocardiogram digital samples and generates characterizing data indicative of the physiology of the heart. Because the cardiac monitor circuitry 40 is implantable, it is preferably powered by a depletable power source such as a battery. To conserve on battery power, the microprocessor 92 only processes data at selected times, as for example, between heart beats. When the microprocessor 92 processes data, the RC oscillator 110 provides the microprocessor 92 with clock pulses to control the execution rate of the microprocessor 92. When the microprocessor is not processing data, the RC oscillator 110 is selectively turned off.

To "wake-up" the microprocessor 92, to permit the microprocessor 92 to process data, the R wave detector 96 detects an R wave from the first channel, the second channel, or both the first and second channels. After a predetermined time duration following the detection of an R wave, the R wave detector 96 provides a trigger signal to the interrupt request 98. The interrupt request 98 services the trigger signal to cause the microprocessor 92 to start the RC oscillator 110 and commence processing data. The predetermined time period or delay in providing the trigger by the R wave detector 96 may be, for example, a period of 300 milliseconds, for example, following the R wave detection to cause the microprocessor 92 to commence processing data prior to the next heart beat. As a result, in accordance with this preferred embodiment, the random access memory 84 need only store the electrocardiogram data for a single electrocardiogram for each of the four channels. After the processing of the electrocardiogram data, the new electrocardiogram digital samples for the next heart beat may be utilized to write over the electrocardiogram data stored during the previous heart beat. However, as will be seen hereinafter, at times digital samples of selected electrocardiograms are to be more permanently stored for later retrieval by the cardiologist. In such a case, the digital samples of the electrocardiograms to be more permanently stored will be moved by the microprocessor 92 to a more permanent storage location within the random access memory 84 prior to the occurrence of the next heart beat. The more permanently stored electrocardiograms may be the electrocardiograms occurring at the onset and termination of various arrhythmic episodes such as ventricular tachycardia or ischemic episodes.

The patient alarm 114 is provided to alert the patient to a low battery condition, a serious arrhythmic event, or a serious ischemic event and to notify the patient that the patient should call the cardiologist. The patient alarm 114 may take the form of a piezo electric buzzer for example or a low energy stimulus which may be felt by the patient but not of sufficient energy to stimulate the heart. Such alarms may also be coded to permit the patient to inform the cardiologist as to the type of event which prompted the alarm.

For programming the modalities of the cardiac monitor, the receiver 102 receives a signal generated externally. The programming signal may be coded in a known manner to define the modality of the cardiac monitor and to set certain operating conditions such as heart rate threshold levels or ST segment deviation threshold levels for detecting ischemia. The programming signals received by receiver 102 are decoded by the program access decoder 104 and conveyed to the interrupt request 98. The interrupt request 98 services the decoded programming signals and provides the same to the microprocessor 92. The microprocessor 92 then stores the programing operating conditions in the random access memory 84 and is also conditioned for fetching only those program instructions from the random access memory 84 for executing the programmed modalities. For example, the random access memory 84 may store a first set of operating instructions to cause the microprocessor to detect arrhythmias and a second set of operating instructions to cause the microprocessor to detect ischemia. If the microprocessor 92 is only programmed for detecting and monitoring arrhythmias, it will only access the first set of operating instructions. If the microprocessor 92 is only programmed for detecting and monitoring ischemia, it will only access the second set of operating instructions. If the microprocessor is programmed for detecting and monitoring both arrhythmias and ischemia, it will access both the first and second sets of operating instructions.

To transmit the characterizing data generated by the microprocessor 92 to an external receiver, the telemetry output 106 may include a radio frequency transmitter of the type well known in the art which transmits a radio frequency carrier which is pulse code modulated. The radio frequency signal generated by the telemetry output 106 is radiated from an antenna such as antenna coil 116. A preferred location of the telemetry antenna coil 116 for efficiently conveying the characterizing data to an external receiver will be described subsequently.

Lastly, the battery monitor 112 monitors the voltage of the battery which powers the cardiac monitor. When the battery voltage decreases to a threshold limit, the battery monitor 112 will provide a signal to the microprocessor 92 indicating that battery power will soon be depleted. In response to such a signal, the microprocessor 92 may cause the patient alarm 114 to provide a suitable alarm to the patient to prompt the patient to notify the cardiologist of the low battery condition. In addition, the microprocessor 92 may store the battery condition in the random access memory 84 and time stamp the low battery condition so the cardiologist upon retrieving the characterizing data from the random access memory will be informed as to the time in which the battery monitor 112 first detected the low battery condition.

Figure 3A:
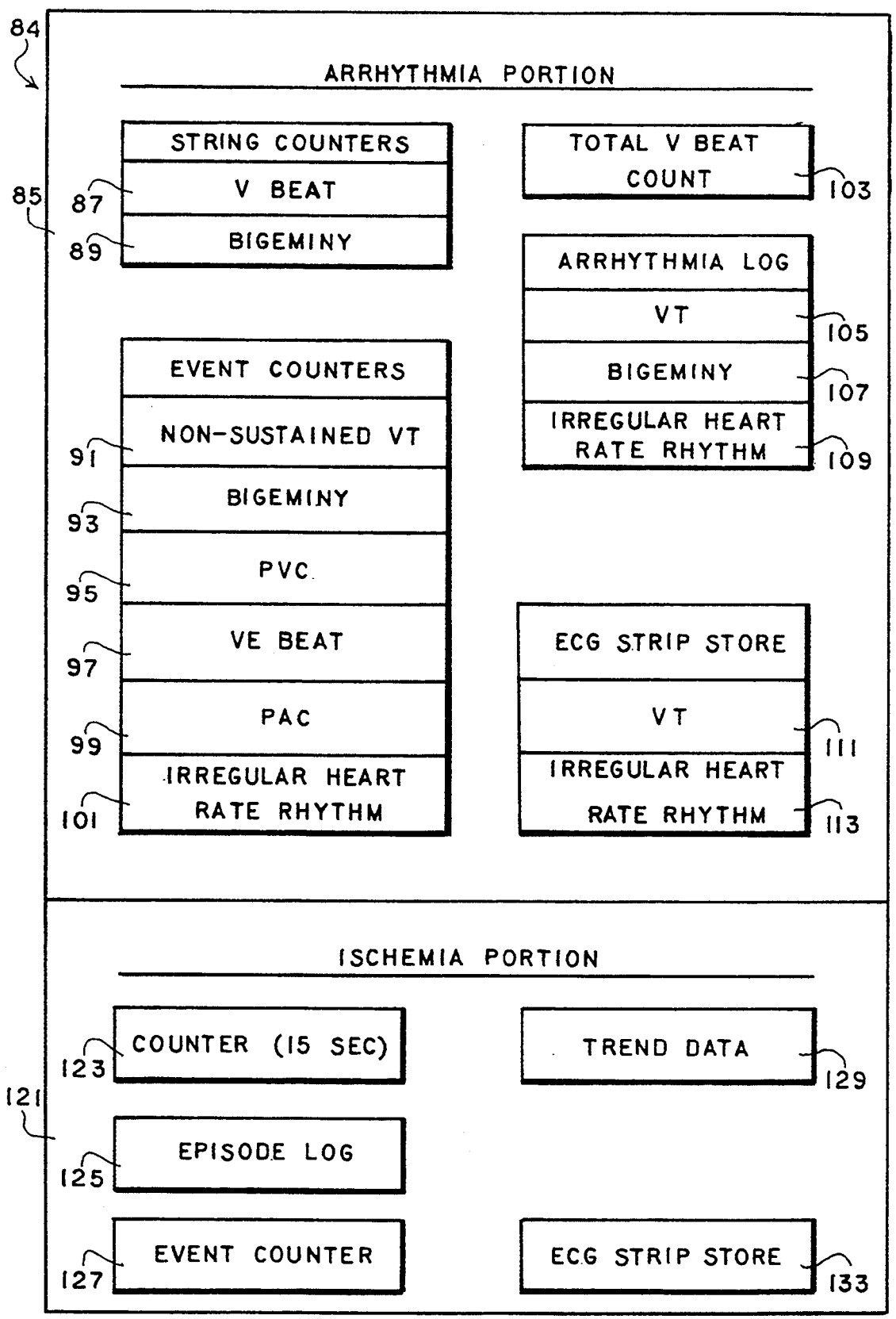
FIG. 3A is a more detailed block diagram of the random access memory of FIG. 3 illustrating the parameters stored within the random access memory for arrhythmia analysis and ischemia analysis in accordance with the preferred embodiment of the present invention.

Referring now to FIG. 3A, it illustrates in greater detail, the random access memory 84 illustrated in FIG. 3. In addition to storing the operating instructions for the microprocessor, the random access memory 84 includes reserved storage locations for storing various types of arrhythmia and ischemia data. The random access memory 84 may be divided into an arrhythmia portion 85 and an ischemia portion 121. The arrhythmia portion includes a ventricular beat string counter 87 for maintaining the number of consecutively occurring ventricular beats and a bigeminy string counter 89 for maintaining a count of the number of consecutive cycles of a bigeminy rhythm. The arrhythmia portion 85 further includes a plurality of event counters including a nonsustained ventricular tachycardia event counter 91, a bigeminy event counter 93 and a premature ventricular contraction (PVC) event counter 95. The event counters further include a ventricular ectopic beat event counter 97, a premature atrial contraction (PAC) event counter 99, and an irregular hear rhythm event counter 101. All of the event counters are utilized for maintaining trend data with respect to the arrhythmias detected and analyzed by the implantable cardiac monitor.

The arrhythmia portion 85 further includes a total ventricular beat counter 103. This counter maintains a count of the total ventricular beats which are detected over a given time period, such as, each hour. The arrhythmia portion 85 further includes an arrhythmia log for recording and time stamping sustained arrhythmia episodes. The arrhythmia log includes ventricular tachycardia event data 105, bigeminy event data 107, and irregular heart rhythm event data 109. When data is stored in the arrhythmia log, it is made available for telemetry to the cardiologist for retrieval. The data stored in the arrhythmia log is time stamped so that the cardiologist will be advised as to the date and time in which the sustained arrhythmic episodes occurred. Lastly, the arrhythmia portion 85 includes a plurality of ECG strip stores including a ventricular tachycardia strip store 111 and an irregular heart rhythm strip store 113 which would include heart beat variability or pauses. When these sustained rhythms are recorded in the arrhythmia log, the cardiac monitor will also move ECG data which is stored in the random access memory 84 in temporary stores to the more permanent ECG strip stores. The ECG data stored in the ECG strip stores may correspond to the ECG data generated at the onset of a ventricular tachycardia or irregular heart rhythm and the ECG data generated during the termination of the ventricular tachycardia.

The ischemia portion 121 includes a counter 123 which is incremented each time ischemia is detected. The counter 123 therefore forms an ischemia timer with which the duration of an ischemia episode may be maintained. The ischemia portion further includes episode log 125 wherein ischemic episode data is maintained. Such data may include ST segment level data for the onset of ischemia, for the peak of the ischemia, and the termination of the ischemia, for example. The ischemia portion 121 also includes an event counter 127 which keeps track of the number of ischemic events which have occurred. Trend data is stored in an ischemia trend data store portion 129. This trend data may be the number of ischemic episodes occurring during each hour for example. The ischemia episode log 125 may be utilized for storing ST level trend data for retrieval by the cardiologist. Lastly, the ischemia portion 121 includes an ECG strip store 133 for storing the ECG data generated at the onset of a sustained ischemic episode, for storing the ECG data generated during the peak of the ischemic episode, and the ECG data generated at the termination of the sustained ischemic episode.

Figure 4:
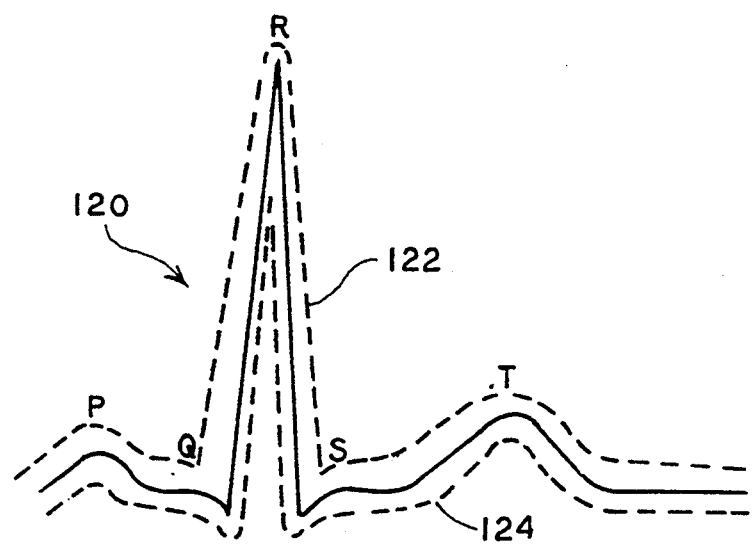
FIG. 4 is a graphic representation of a template which is generated and utilized by the implantable cardiac monitor of FIG. 3 for discriminating between normal and abnormal heart beats in accordance with the present invention.

One important function performed by the processing means 90 in processing the electrocardiogram data samples of each natural heart beat is the discrimination between a normal sinus heart beat and an abnormal heart beat herein referred to as a ventricular beat. More specifically, the abnormal heart beat is an ectopic ventricular heart beat wherein the heart beat originates in the ventricles rather than at the sinus node where a normal heart beat originates. Such a ventricular heart beat is characterized by an R wave having a longer duration than the R wave of a normal sinus heart beat. In order to facilitate the discrimination between a normal sinus heart beat and a ventricular beat, the microprocessor 92 of the processing means 90 establishes a template corresponding to the electrocardiogram of a normal sinus heart beat of the patient. The microprocessor 92 generates such a template upon the initialization of the cardiac monitor and, in accordance with the present invention, revises the template at spaced apart time intervals to account for changes in the normal morphology of the patient's heart over time. Such revisions to the template may be made at periodic intervals of, for example, 15 seconds, or alternatively may be made after a predetermined number of heart beats have occurred, such as, for example, 15 heart beats. In generating the template, the microprocessor averages a first predetermined number of data samples for each data point for a corresponding number of electrocardiograms and ascribes to each data point a maximum limit and a minimum limit. Such a template 120 is illustrated in FIG. 4. The maximum limits are denoted by the dashed line 122 and the minimum limits are denoted by the dashed line 124. While the template illustrated in FIG. 4 expands the entire electrocardiogram, in accordance with the present invention, the template 120 may span only the QRS portion of the electrocardiogram.

To determine if a heart beat is a normal sinus heart beat or an abnormal heart beat, the stored data samples of the electrocardiogram being processed are aligned with the template. Then, the deviation between the data samples of the electrocardiogram being processed and the template for each data point are summed in a running total until each data sample of the electrocardiogram being processed has been compared to the template. Thereafter, the running sum is normalized to derive a number indicative of the difference between the electrocardiogram being processed and the template. If that number is greater than a predetermined threshold, the heart beat corresponding to the electrocardiogram being processed is classified as an abnormal heart beat. Conversely, if that number is less than the predetermined threshold, the heart beat corresponding to the electrocardiogram being processed is classified as a normal sinus heart beat.

The foregoing discrimination or classification of the normal heart beats and the abnormal heart beats is utilized for classifying heart beat rhythms as will be seen hereinafter and for detecting and monitoring ischemia. More specifically, the microprocessor 92 processes only those electrocardiograms corresponding to normal sinus heart beats for the purpose of detecting and monitoring ischemia.

In accordance with the present invention, the template 120 is revised at spaced apart time intervals such as periodically every 15 seconds. After 15 seconds has elapsed since the last template revision, the microprocessor averages the data samples for only those electrocardiograms corresponding to classified normal sinus heart beats and then computes a weighted average which is then averaged with the previous template. As a result, revisions to the template will accurately represent the gradual changes in heart morphology of a patient over time. The incorporation of an adaptive template by the revisions to the template as described above is an important advancement in the art and is considered to be one important element in rendering an implantable cardiac monitor for detecting and monitoring arrhythmias and ischemia a reality.

Figure 5:
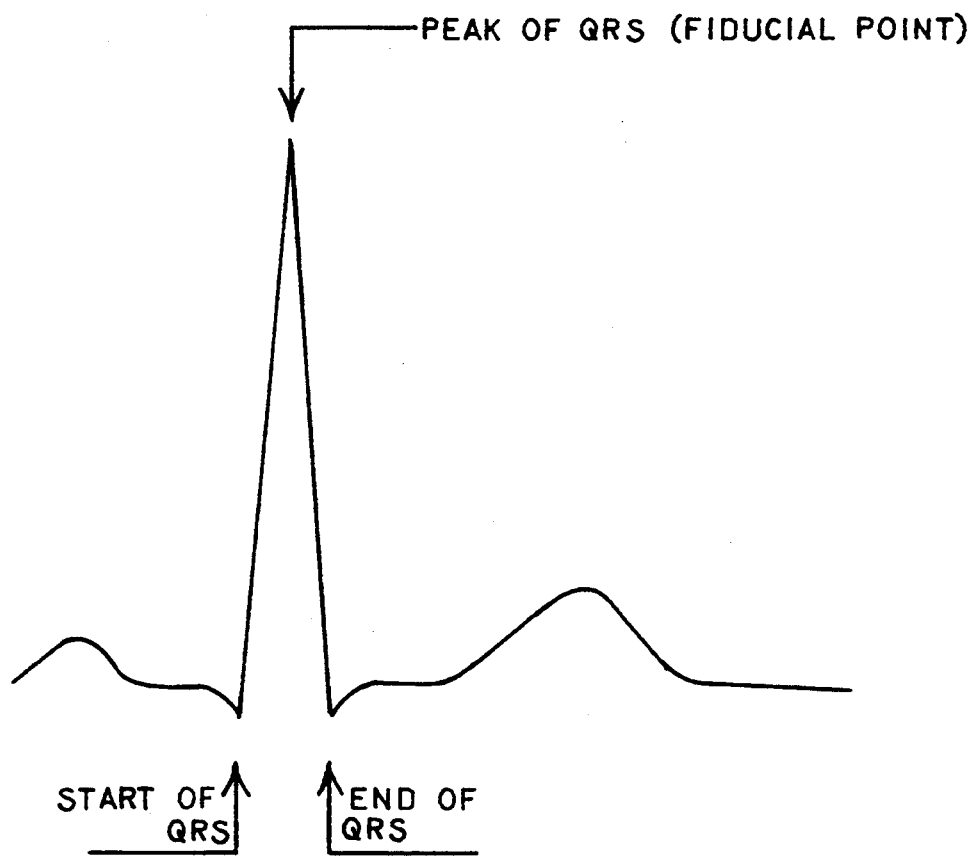
FIG. 5 is another graphic representation of a typical, normal ECG waveform showing fiducial reference points determined by the implantable cardiac monitor of FIG. 3 in accordance with the present invention for analyzing arrhythmias of the heart.

Referring now to FIG. 5, it provides another graphic representation of a typical, normal ECG wave form showing fiducial reference points which the processing means 90 determines and utilizes for detecting and monitoring arrhythmias of the heart. The electrocardiograms of only the first and second channels are processed for distinguishing between normal sinus heart beats and abnormal sinus heart beats and for detecting and monitoring arrhythmias. The processing means 90 determines three fiducial points for detecting and monitoring arrhythmias. The three fiducial points are the start of the QRS complex, the end of the QRS complex, and the peak of the QRS complex which are determined in that order. When the microprocessor 92 begins processing the data samples of the electrocardiograms in response to the delayed signal from the R wave detector 96, the microprocessor in knowing the delay time of the trigger signal can determine approximately when the R wave was detected by the R wave detector 96. The microprocessor establishes an interrogation window which is wide enough to encompass the QRS complex. To determine the three fiducial points, the microprocessor 92 performs a band pass differentiating function upon the stored ECG data which eliminates the P wave and the T wave from the ECG and performs slope discrimination of the QRS complex. The start of the QRS complex is determined by the beginning of a rapidly increasing slope and the end of the QRS complex is determined by the end of a rapidly decreasing slope. After the first two fiducial points are determined, the microprocessor 92 then determines when the slope of the QRS complex transitions from a rapidly increasing slope to a rapidly decreasing slope. This point of transition denotes the peak of the QRS complex. By determining these three fiducial points, the microprocessor 92 is then able to line up the data points of the ECG wave forms corresponding to the heart beat being processed with the template as previously described and illustrated in FIG. 4 for comparing the ECG wave forms being processed with the template. Also, from these fiducial points, the microprocessor 92 is able to determine the duration of the QRS complex and for determining the R to R interval from the last processed heart beat for determining heart rates.

Figure 6:
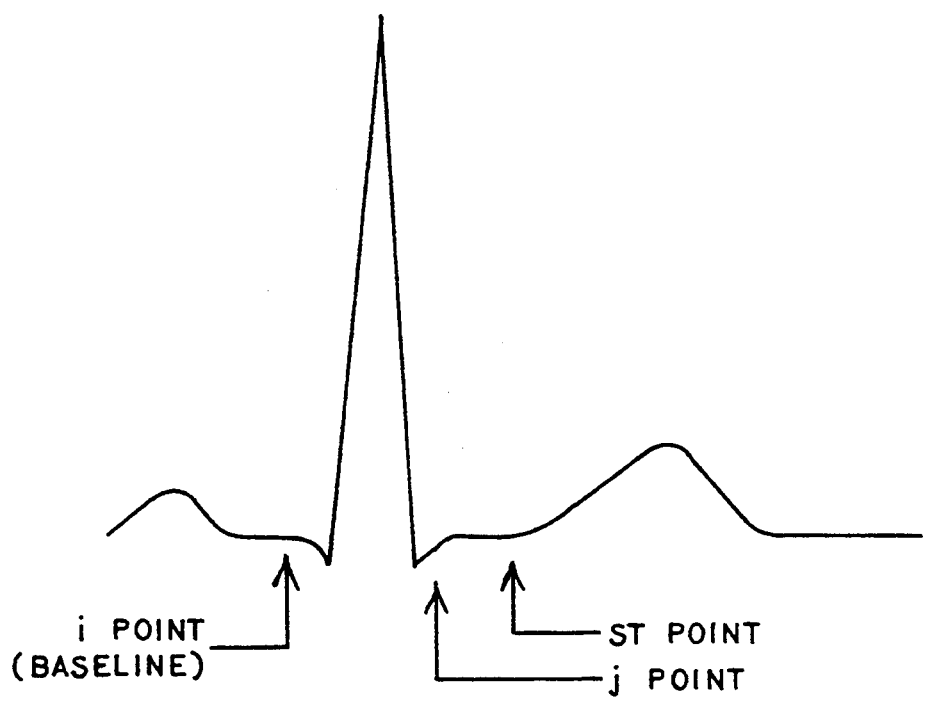
FIG. 6 is another graphic representation of a typical or normal ECG waveform showing fiducial reference points determined and used by the implantable cardiac monitor of FIG. 3 in accordance with the present invention for analyzing ischemia.

Referring now to FIG. 6, it illustrates another graphic representation of a typical or normal ECG wave form showing the fiducial points determined by the microprocessor 92 for detecting and monitoring ischemia. Again, the microprocessor determines three fiducial points, the i point, the j point, and the ST point. In performing this operation, the microprocessor processes the digital samples of the ECG wave forms of all four channels, namely, the first, second, third, and fourth channels. For each of the electrocardiograms of these channels, the microprocessor, from the stored digital samples, determines the i point as the flat portion known as the isoelectric prior to the first negative deflection which is the Q wave before the QRS complex. The j point is determined from the first deflection from the S wave and the ST point is determined to be the point in the electrocardiogram spaced from the j point by some predetermined interval, for example, 80 milliseconds. The i point is utilized for establishing the baseline for the ischemia determinations. The ST point is the point in which the deviation from the baseline at the i point is determined for detecting ischemia.

Figure 7:
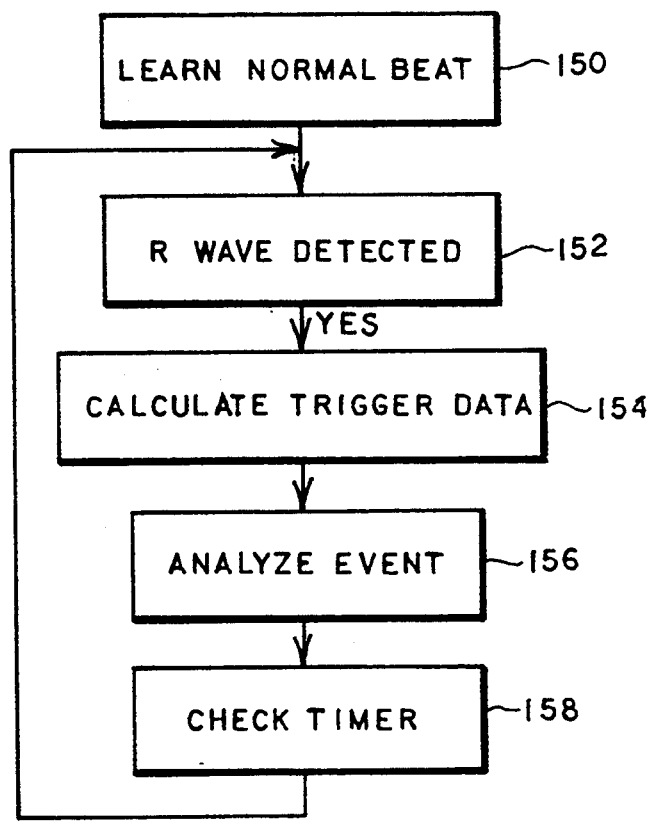
FIG. 7 is an overall flow diagram illustrating the manner in which the implantable cardiac monitor of FIG. 3 may be implemented for monitoring the physiology of the human heart.

Referring now to FIG. 7, it is an overall flow diagram illustrating the manner in which the implantable cardiac monitor of FIG. 3 may be implemented for monitoring the physiology of the human heart. Upon initialization, the microprocessor in step 150 establishes the initial template as previously described, of the type as illustrated in FIG. 4, to be utilized for discriminating between normal sinus heart beats and ventricular beats. Once the microprocessor stores the initialized template in the random access memory 84, the microprocessor 92 waits for the delayed signal from the R wave detector 96 indicating that an R wave had been detected by the electrodes associated by one or both of the first and second channels. As illustrated in FIG. 7, the microprocessor 92 receives the delayed signal from the R wave detector 96 in step 152.

After receiving the delayed signal from the R wave detector 96 indicating that an R wave had been detected, the microprocessor then in step 154 calculates necessary trigger data. In this step, the microprocessor determines from the current time when the R wave detector 96 must have detected the R wave. The microprocessor is able to discern the time in which the R wave had been detected by the R wave detector 96 because the delay in providing the R wave signal to the microprocessor is a constant delay stored in memory. The trigger point, that is the time in which the R wave detector 96 detected the R wave, is later utilized by the microprocessor for establishing time windows in which it analyzes the ECG data for the heart beat which had been stored in the random access memory 84 through the direct memory access 88 prior to receiving the delayed signal from the R wave detector 96.

Upon receipt of the interrupt from interrupt request 98 corresponding to the delayed signal from the R wave detector 96, the microprocessor then proceeds to step 156 to analyze the event or heart beat. The execution in analyzing the event or heart beat is denoted by the general reference character 156 and, as will be seen hereinafter, requires a number of executions which are illustrated in the flow diagrams of FIGS. 8 through 13 which will be described hereinafter. Generally, in analyzing the event, the microprocessor 92 performs such functions as determining if there was noise in the first and second channels while the ECG data was stored in the random access memory 84, the microprocessor verifies that the first and second channels have ECG data stored therein representing a QRS complex, and the microprocessor determines the fiducial points in the stored ECG data as previously described with respect to FIG. 5. The microprocessor in analyzing the event further classifies the heart beat as a normal sinus heart beat or a ventricular beat by comparing the stored ECG data to the template stored in the random access memory 84. After determining whether the heart beat was a normal sinus heart beat or a ventricular beat, the microprocessor then classifies the heart rhythm based upon the currently analyzed heart beat and previous heart beat history as will be described subsequently.

After analyzing the event or heart beat, the microprocessor then enters a check timer routine at step 158. The check timer routine is illustrated in detail in the flow diagrams of FIGS. 14 through 16 which will also be described subsequently. Generally, during the check timer routine, the microprocessor determines if a time period had elapsed since last performing the check timer routine. If sufficient time has elapsed, the microprocessor revises the template currently stored in the random access memory 84, determines the fiducial points illustrated in FIG. 6 for detecting and analyzing ischemia, and then performs the ischemia analysis. Once the check timer routine is completed the microprocessor returns and is deactivated until it receives another delayed R wave detection signal from the R wave detector 96.

Figure 8A:
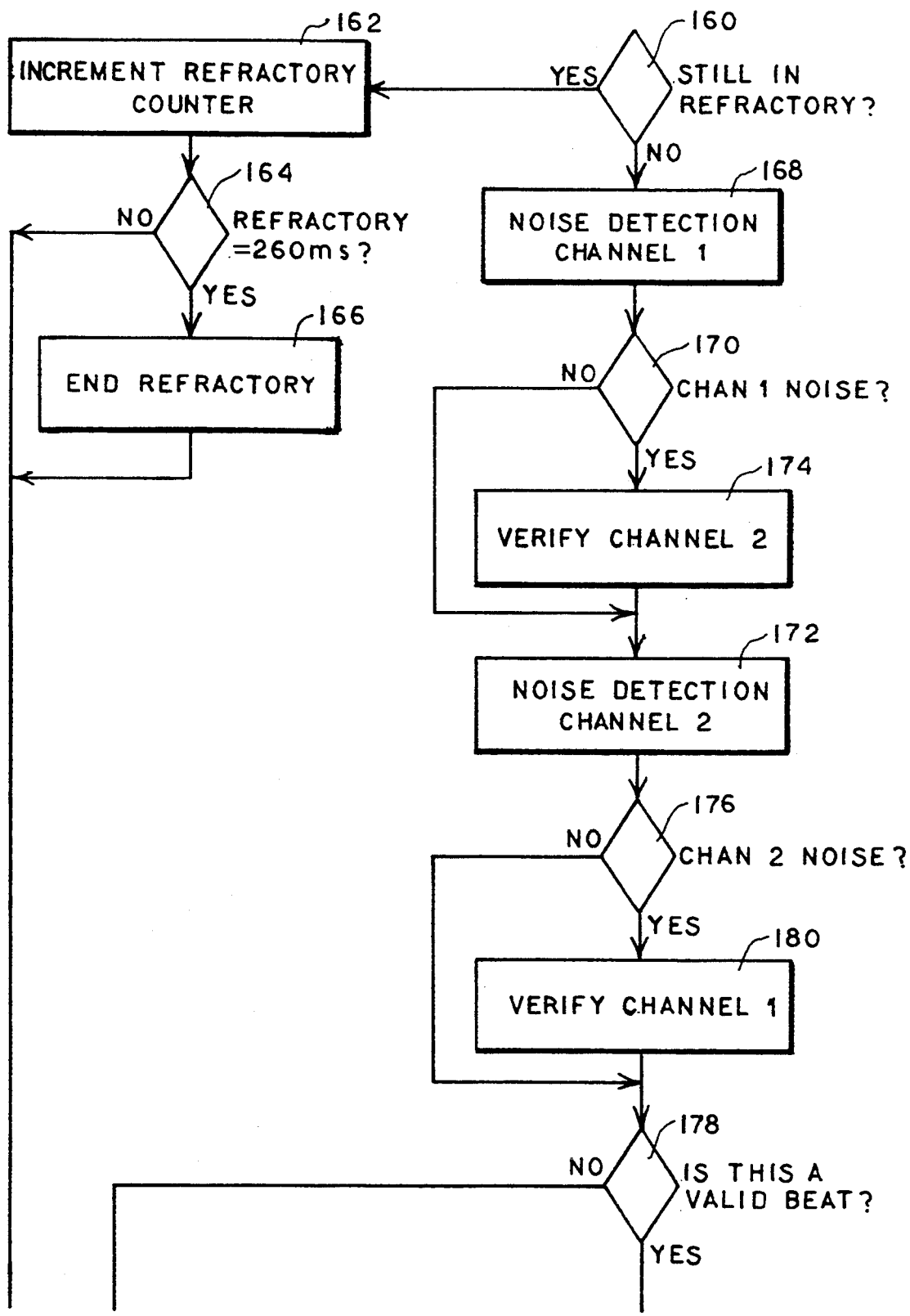
FIGS. 8A and 8B when taken together are a flow diagram illustrating the manner in which the implantable cardiac monitor of FIG. 3 may be implemented for analyzing a heart beat in accordance with the present invention.
Figure 8B:
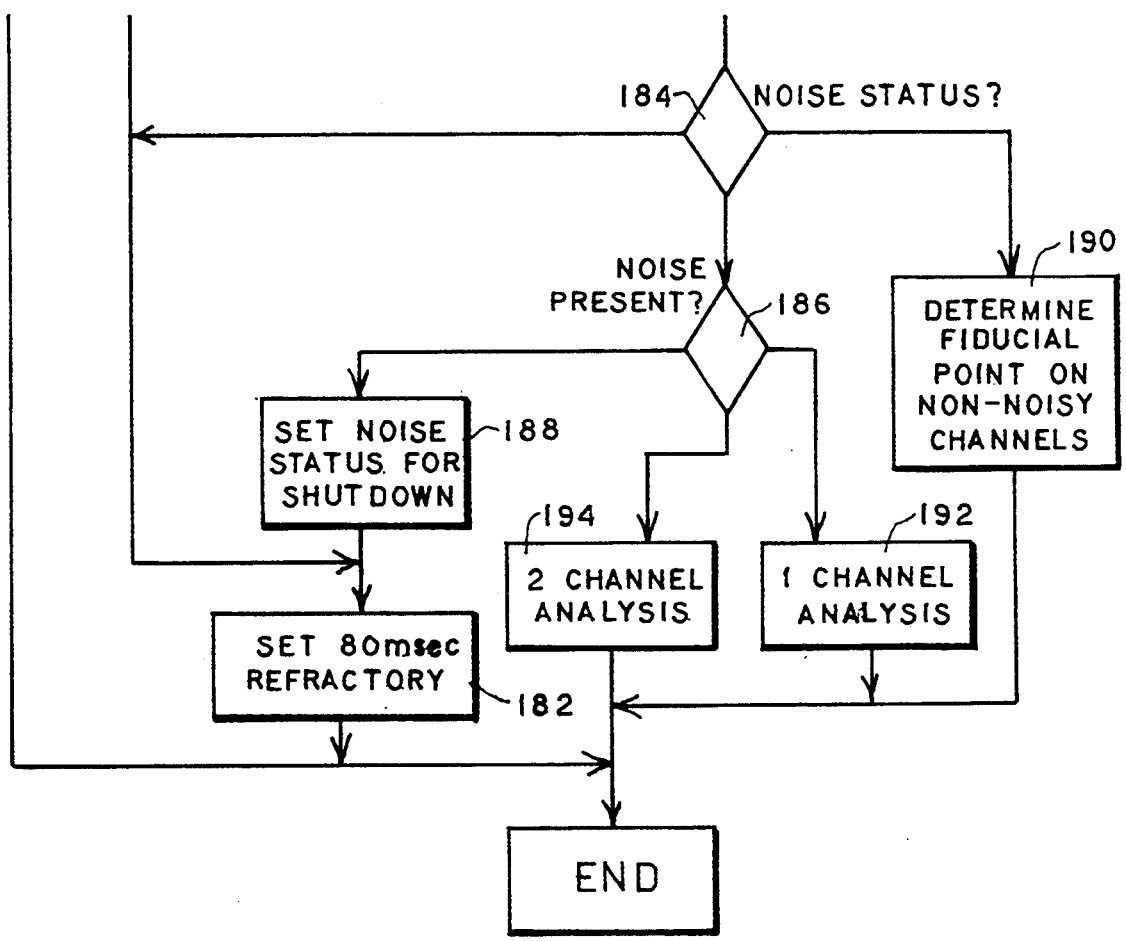

Referring now to FIGS. 8A and 8B, these figures when taken together are a flow diagram illustrating the manner in which the implantable cardiac monitor of FIG. 3 may be implemented for analyzing an event or heart beat as generally illustrated at step 156 in FIG. 7. After determining the trigger point, the point in time in which the R wave detector 96 detected an R wave, the microprocessor 92 first determines in step 160 if it is still in refractory. Even though the microprocessor 92 is not processing data during the heart beats of the heart, the crystal oscillator 108 in performing its real time clock function permits the microprocessor to maintain a refractory counter which is utilized by the microprocessor to determine if enough time has elapsed since the last heart beat for the current heart beat to be analyzed to be a valid heart beat. In other words, if the present trigger point occurred too soon after the immediately preceding trigger point, the microprocessor 92 will know that the R wave detected by the R wave detector 96 cannot be a valid R wave of a QRS complex. The refractory period established by the microprocessor 92 may be programmable and on the order of 260 milliseconds. If the circuitry determines that it is still in refractory, it then increments the refractory counter in step 162. After incrementing the refractory counter, the circuitry determines if the refractory period kept in the refractory counter is now equal to the refractory period of 260 milliseconds. If it is not, signals from the R wave detector 96 are ignored. However, if the refractory time kept in the refractory counter after having been incremented is now equal to the refractory period of 260 milliseconds, the microprocessor in step 166 sets a bit in the random access memory 84 indicating the end of refractory and then returns and terminates processing until the receipt of another delayed R wave detector signal from the R wave detector 96. The bit set in the random access memory 84 will then be utilized the next time the microprocessor 92 executes step 160 in determining whether it is still in refractory.

If in performing step 160 the microprocessor 92 determines that it is not in refractory, it then proceeds to step 168 to detect for noise in the ECG data stored in the random access memory 84 obtained from the first channel. In performing step 168 the microprocessor 92 generates data to permit it to determine if there was such noise in the first channel. Such data may result from analyzing the ECG data stored in the random access memory 84 obtained from the first channel for zero crossings indicated by the data which would not normally occur during portions of a valid heart beat. For example, the microprocessor 92 analyzes the stored data for zero crossings at times which correspond to the ST segment of the ECG wherein, if the heart beat is a valid heart beat, the data would indicate a generally constant level. However, if there was noise in the first channel, the microprocessor will detect zero crossings resulting from signals of changing directions which would not normally occur during this interval.

After generating the noise data from step 168, the microprocessor then determines if there was noise in the first channel when the data was stored in the random access memory 84. The microprocessor makes this determination at step 170. If it is determined that there was no noise in the first channel, the microprocessor then proceeds to step 172 to perform the noise detection analysis with respect to the data stored in the random access memory which was obtained from the second channel. However, if there was noise in the first channel, the microprocessor then proceeds to step 174 to verify that the data stored in the random access memory 84 and obtained from the second channel indicates that there was a valid QRS complex in the second channel. Preferably this is accomplished by discerning if the data stored in the random access memory 84 obtained from the second channel was above a given threshold. The verification of a QRS complex in the second channel is performed to take into account the situation where there is noise in the first channel and no signal detected in the second channel which indicates that the original R wave detection was due to a noise artifact in the first channel.

After generating the noise detection data from the second channel in step 172, the microprocessor then in step 176 determines if there was noise in the second channel when the data from the second channel was stored in the random access memory 84. If it is determined that there was not noise in the second channel, the microprocessor then proceeds to step 178 to determine if there was a valid heart beat detected. If it is determined that there was noise in the second channel, the microprocessor then performs step 180 to verify the detection of a QRS complex in the first channel. In performing step 180, the microprocessor performs the same executions as it did in step 174 but in this case, it performs these operations upon the data stored in the random access memory 84 obtained from the first channel.

In performing step 178 to determine if a valid beat had been detected, the microprocessor utilizes the following criteria. If both the first and second channels contained noise, the microprocessor will determine that a reliable beat classification cannot be performed. If the microprocessor detected that there was noise in one channel and was unable to verify a detected QRS complex in the other channel, it will determine that a valid beat had not been detected. As a result, if in step 178 the microprocessor determines that a valid beat had not been detected, it will set in step 182 another refractory period of, for example, 80 milliseconds. This precludes the microprocessor from processing any more data until after this new refractory period has elapsed. This provides sufficient time for any noise in the first and second channels to settle down before the microprocessor once again processes data period.

Even though the microprocessor may determine in step 178 that there was a valid heart beat detected, such a determination is considered conditional by the microprocessor and the microprocessor will make note of certain characteristics by setting appropriate bits in the random access memory 84 relating to the characteristics detected in the data obtained from the first and second channel. For example, if the microprocessor finds that either or both channels included noise even though the threshold had been exceeded, it will make note of the noise on these channels. In addition, the bits which are set denoting the detected noise will be utilized in analyzing the next event as noise history in a manner to be seen hereinafter. The foregoing is best illustrated in the next step performed by the microprocessor, which is step 184. In step 184 the microprocessor determines the noise status based upon prior noise history. If noise was previously detected in the data stored for the previous heart beat, and if noise is still present, the microprocessor will proceed to step 182 to set the new refractory period. If noise had not been previously detected with respect to the previously detected heart beat, the microprocessor proceeds to step 186 to determine the present noise conditions. If there is noise in the stored data of both the first and second channels, the microprocessor then in step 188 sets the noise status for shutdown. During shutdown, the microprocessor does not process anymore data, as, for example, determining the previously mentioned fiducial points. After shut down, the microprocessor proceeds to step 182 to set the new 80 millisecond refractory period.

If in step 184 the microprocessor determines that it had previously been in shutdown but that a valid beat had been detected, then the microprocessor proceeds to step 190 to determine the fiducial points illustrated in FIG. 5 for the data stored in the random access memory 84 and obtained from the first and second channels which did not contain noise. The reason for the microprocessor determining these fiducial points before exiting is to enable the microprocessor to determine a heart rate for the next detected heart beat. A heart rate could not be detected for the present beat since the microprocessor had previously detected noise in both the first and second channels and therefore could not determine the required fiducial points.

In step 186, the microprocessor also determines if both the first and second channels did not contain noise or if only one channel contained noise. If one channel contained noise, the microprocessor proceeds to step 192 to perform a channel analysis only with respect to the data obtained from the channel having no noise. If both the first and second channels contained data without noise, the microprocessor proceeds to step 194 to perform channel analysis on both the first and second channels.

Figure 9:
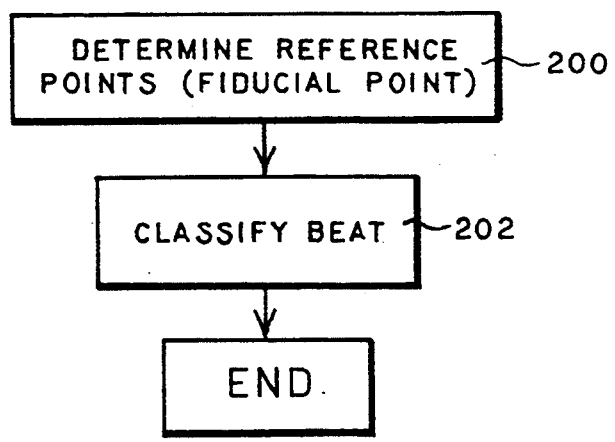
FIG. 9 is an overall flow diagram illustrating the manner in which the implantable cardiac monitor of FIG. 3 may be implemented for performing the channel analysis of the flow diagram of FIGS. 8A and 8B in accordance with the present invention.

Referring now to FIG. 9, it is an overall flow diagram illustrating the manner in which the implantable cardiac monitor of FIG. 3 may be implemented for performing the channel analysis of the flow diagram of FIGS. 8A and 8B in accordance with the preferred embodiment. As previously mentioned, the microprocessor 92 performs the channel analysis upon the data stored in the random access memory 84 obtained from either or both of the first and second channels depending upon the detected noise conditions of the stored data. As a result, the channel analysis may be performed on either the first channel data or the second channel data or upon both the data obtained from the first and second channels.

The channel analysis basically includes the steps 200 and 202 wherein, in step 200, the microprocessor determines the fiducial points illustrated in FIG. 5 and, where, in step 202, the microprocessor classifies the detected heart beat. Step 200 to determine the fiducial points will be described hereinafter with respect to FIG. 10 and step 202 will be described hereinafter with respect to the flow diagrams of FIGS. 11 through 13.

Figure 10:
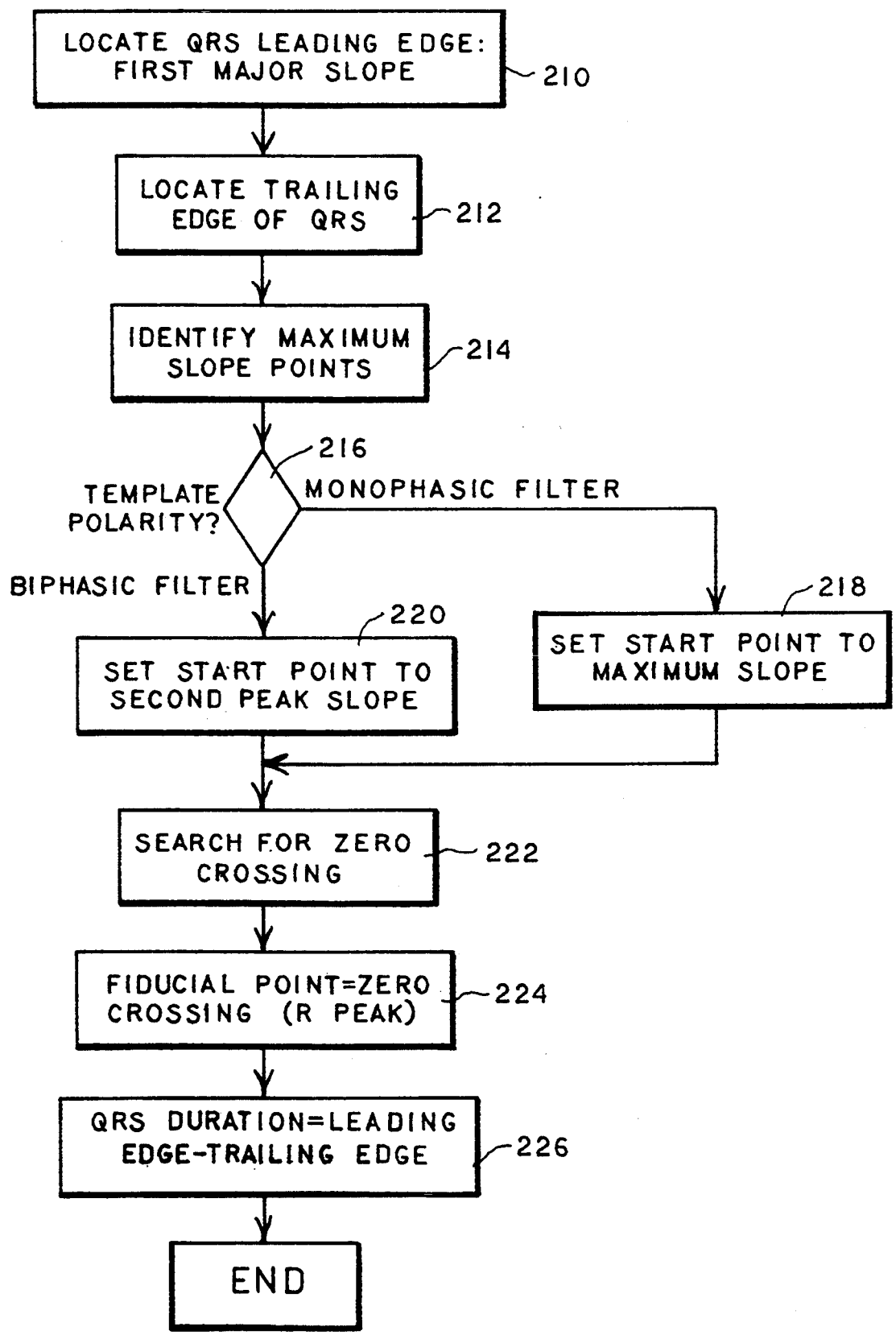
FIG. 10 is a flow diagram illustrating the manner in which the implantable cardiac monitor of FIG. 3 may be implemented for determining the fiducial points illustrated in FIG. 5 in accordance with the present invention.

Referring now to FIG. 10, it is a flow diagram illustrating the manner in which the implantable cardiac monitor of FIG. 3 may be implemented for determining the fiducial points illustrated in FIG. 5 in accordance with this preferred embodiment. As previously mentioned, and as illustrated in FIG. 5, the microprocessor determines three fiducial points for arrhythmia analysis, the three fiducial points being the leading edge of the QRS complex, the trailing edge of the QRS complex, and the peak of the QRS complex.

To locate the three fiducial points, the microprocessor establishes a fiducial window wherein it processes the ECG data stored a predetermined time before to a predetermined time after the trigger point. In accordance with this preferred embodiment, the microprocessor establishes a fiducial window by processing ECG data stored 160 milliseconds before to 100 milliseconds after the trigger point.

The microprocessor, in step 210, first locates the first fiducial point of the QRS complex leading edge. As previously described, the microprocessor accomplishes this by differentiation to find the first major slope preceding the Q wave. Next, in step 212, the microprocessor determines the second fiducial point which is the trailing edge of the QRS complex by differentiation to find the last major slope of the QRS complex. Next, in step 214, the microprocessor 92 identifies the maximum slope points as the first and second fiducial points. Thereafter, in step 216, the microprocessor determines the polarity of the filtered signal of the template. If the template polarity is monophasic, the microprocessor in step 218 sets the template start point as the maximum slope. If however the template polarity is biphasic, the microprocessor in step 220 sets the template start point to the second peak slope.

Following step 220, the microprocessor determines the peak of the QRS complex by first, in step 222, searching for the zero crossing point of the filtered signal of the template. Next, in step 224, the microprocessor processes the ECG data for noting the zero crossing point as the third fiducial point which is the peak of the QRS complex. Lastly, in step 226, the microprocessor computes the duration of the QRS complex by subtracting the time of the leading edge from the time of the trailing edge of the QRS complex.

Figure 11:
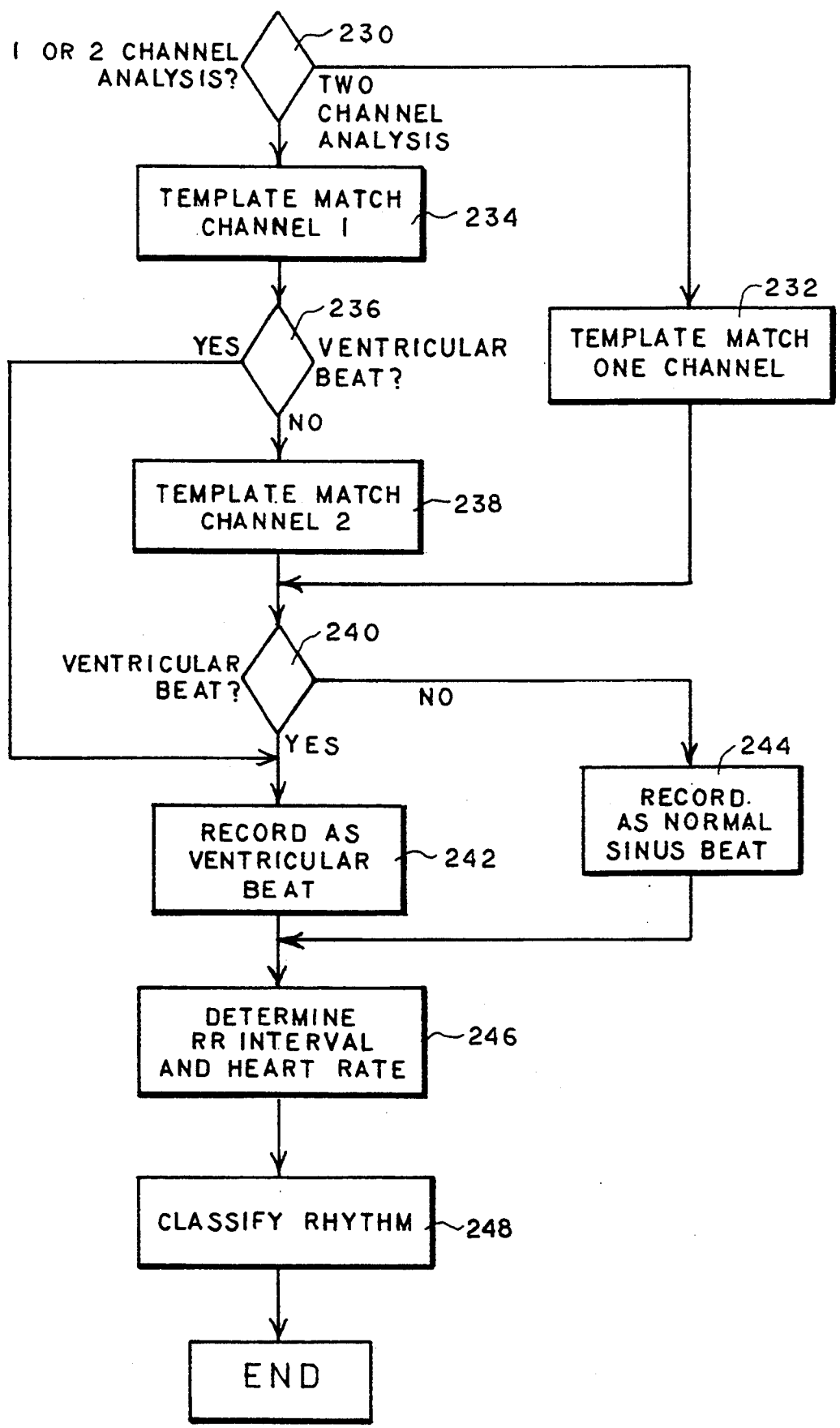
FIG. 11 is a flow diagram illustrating the manner in which the implantable cardiac monitor of FIG. 3 may be implemented for classifying heart beats in accordance with the present invention.
Figure 12:
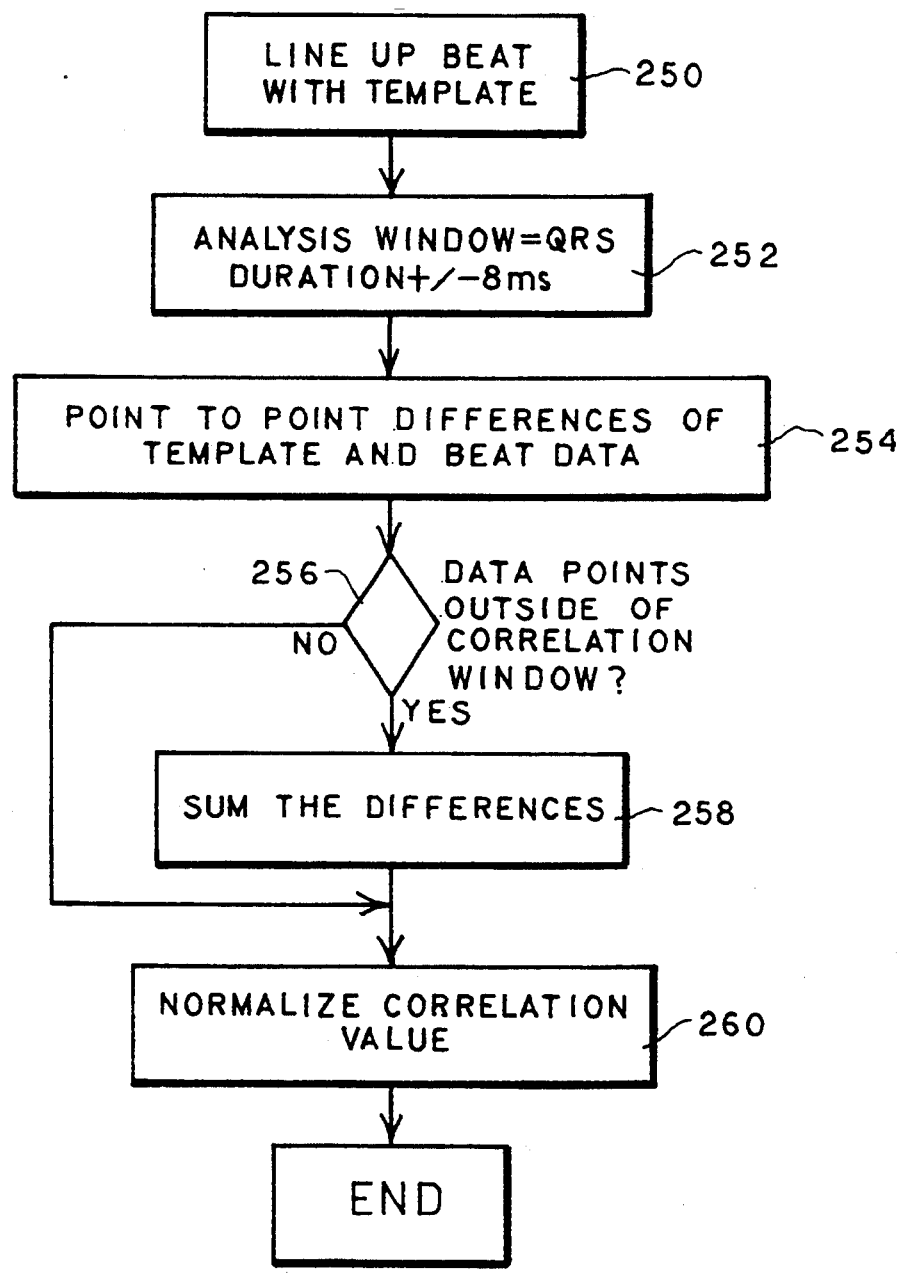
FIG. 12 is a flow diagram illustrating the manner in which the implantable cardiac monitor of FIG. 3 may be implemented for matching a detected ECG to a stored template as illustrated in FIG. 4 in accordance with the present invention.

After determining the fiducial points as described with respect to FIG. 10, the microprocessor then classifies the heart beat as illustrated in the flow diagrams of FIGS. 11 through 13. Referring more particularly to FIG. 11, it is a flow diagram illustrating the manner in which the implantable cardiac monitor of FIG. 3 may be implemented for classifying heart beats in accordance with this preferred embodiment of the present invention. The microprocessor begins at step 230 to classify the heart beats by determining whether it is to perform the beat classification on the data obtained from both the first and second channels or upon the data obtained from only one of the channels. If the microprocessor determines that it is to classify the heart beat on the data obtained from just one of the channels, it will proceed to step 232 to perform the template match to be described hereinafter with respect to FIG. 12 on the data obtained from the one channel. Such one channel analysis will occur when one channel has detected a valid QRS complex and, for example, when the other channel had noise when providing the random access memory 84 with ECG data.

If the microprocessor is to perform channel analysis with respect to the ECG data obtained from both the first and second channels, it will first execute a template match in step 234, to be described hereinafter with respect to FIG. 12, upon the data obtained from the first channel. After performing the template match in step 234 upon the data obtained from the first channel, the microprocessor determines whether the heart beat was a normal sinus heart beat or a ventricular beat. If the heart beat was a ventricular beat, the microprocessor jumps to step 242 to record the heart beat as a ventricular beat. However, if in step 236 the microprocessor determines that the heart beat was a normal sinus heart beat and not a ventricular beat, it will proceed to step 238 to perform the template match upon the data obtained from the second channel. Thereafter, in step 240, the microprocessor determines whether the heart beat was a normal sinus heart beat or a ventricular beat based upon the stored data obtained from the second channel. If the microprocessor had performed a single channel analysis in step 232, it would then go to step 240 to determine, based upon the template match, if the heart beat had been a normal sinus heart beat or a ventricular beat. In either case, if the microprocessor determines in step 240 that the heart beat was a ventricular beat, it would proceed to step 242 to record the heart beat as a ventricular beat. However, if in step 240, the microprocessor determines that the heart beat was a normal sinus heart beat, it would record it in step 244 as a normal sinus heart beat.

After recording the heart beat as a ventricular beat or a normal sinus heart beat, the microprocessor then proceeds to step 246 to calculate the heart rate based upon this last heart beat and a running average heart rate based upon the last predetermined number of normal sinus R to R intervals, such as the last six normal sinus R to R intervals. The microprocessor stores in the random access memory 84 both the heart rate based upon the last heart beat and the running average heart beat. After completing step 246, the microprocessor then proceeds to step 248 for classifying the heart rhythm.

Referring now to FIG. 12, it is a flow diagram illustrating the manner in which the implantable cardiac monitor of FIG. 3 may be implemented for comparing the ECG data stored in the random access memory 84 and obtained from the first channel, the second channel, or both the first and second channels to perform the template match operations to facilitate the classification of the heart beat. In performing the template match operation, the microprocessor first, in step 250, aligns the ECG data with the stored template. In performing this step, the microprocessor aligns the maximum point of the QRS complex with the stored template. Thereafter, in step 252, the microprocessor establishes an analysis window beginning a predetermined time before the QRS complex and ending at a predetermined time following the QRS complex. In accordance with this preferred embodiment, the analysis window begins eight milliseconds before the QRS complex and extends to eight milliseconds after the QRS complex of the stored ECG data. Hence, in accordance with the present invention, in performing the template match operations, the microprocessor compares the QRS complex portion of the stored ECG data with the QRS complex of the stored template.

After establishing the analysis window in step 252, the microprocessor proceeds to step 254 to calculate the point to point differences between the data points of the stored ECG data and the stored ECG template. If the point to point difference exceeds the maximum or minimum limits of the stored ECG template, the microprocessor sums the differences in the random access memory 84.

Following the calculations of the point to point differences between the stored ECG data and the stored ECG template, the microprocessor then in step 260 normalizes the total sum of the differences by dividing the total sum of the differences by some percentage, such as, for example, twenty-five percent (25%) of the integral of the QRS complex of the template to determine a normalized correlation value. If in step 256 it is determined that there are no data points outside of the template, the microprocessor does not calculate the sum of the differences but instead proceeds directly to step 260 for determining the normalized correlation value.

Following the template match operations illustrated in FIG. 12, the microprocessor then, by utilizing the normalized correlation value, classifies the heart beat as either a normal sinus heart beat or an abnormal heart beat herein referred to as a ventricular beat as described previously with respect to FIG. 11. The microprocessor then records the classification of the heart beat in the random access memory 84.

Figure 13A:
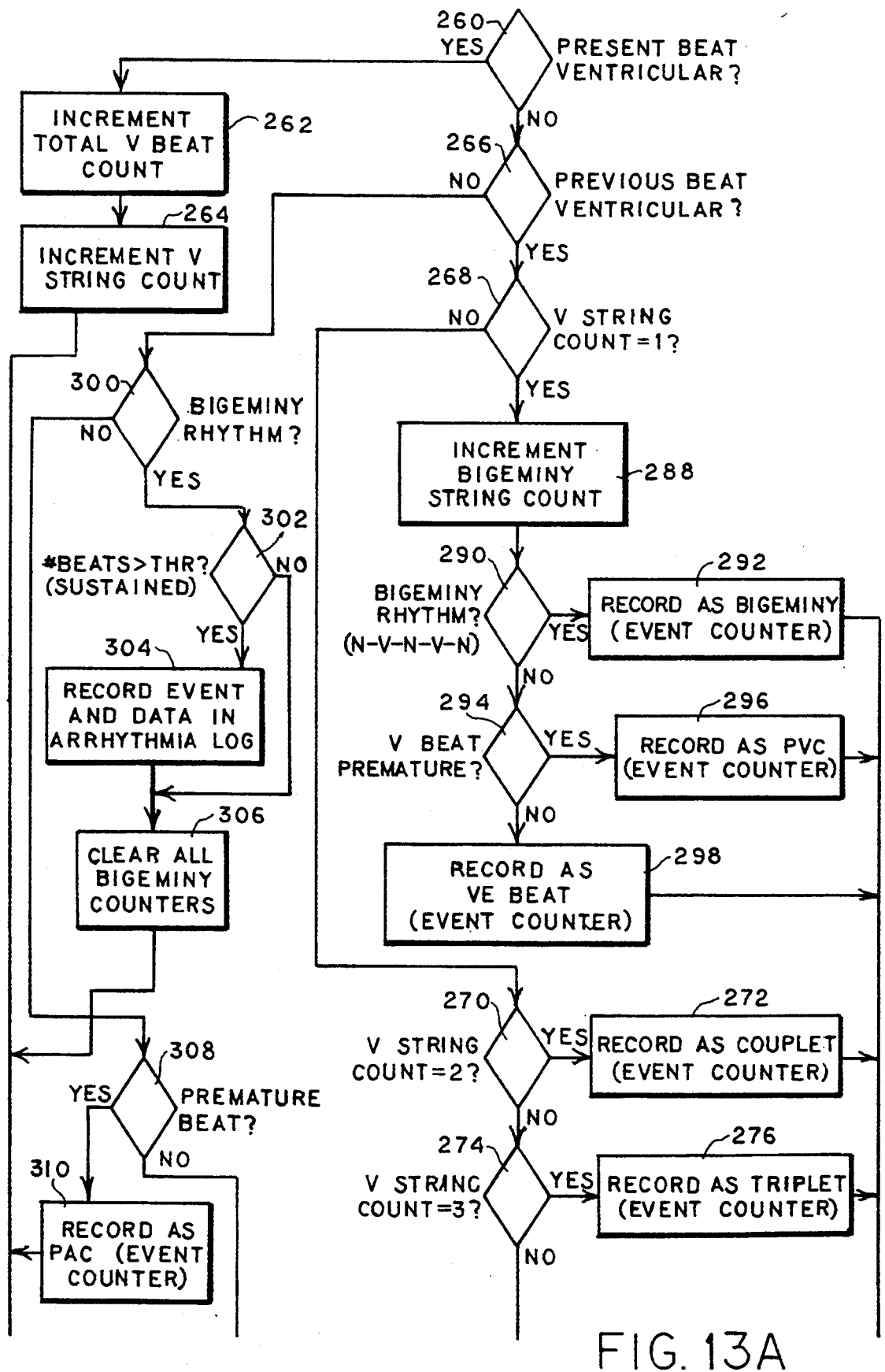
FIGS. 13A and 13B when taken together form a flow diagram illustrating the manner in which the implantable cardiac monitor of FIG. 3 may be implemented for classifying heart beat rhythms in accordance with the present invention.
Figure 13B:
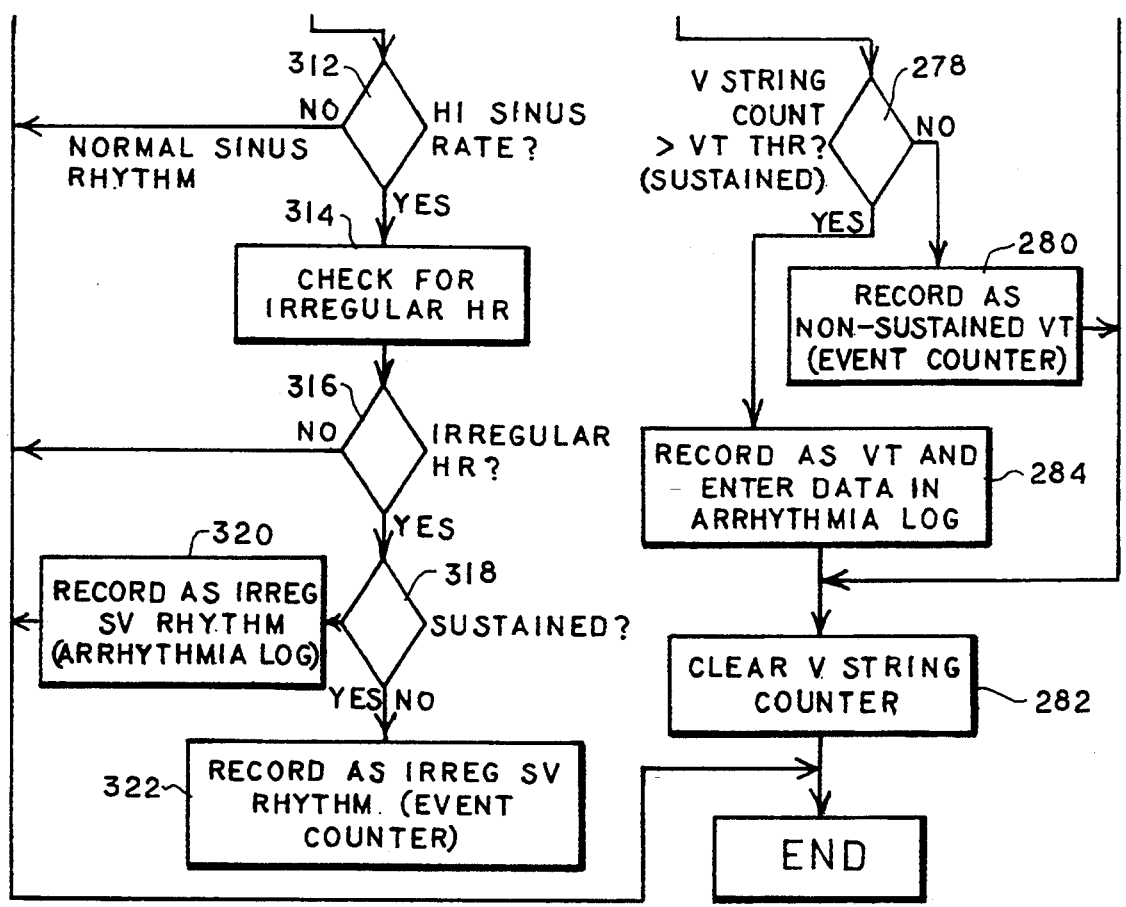

Referring now to FIGS. 13A and 13B, these figures when taken together form a flow diagram illustrating the manner in which the implantable cardiac monitor of FIG. 3 may be implemented for classifying heart beat rhythms in accordance with this preferred embodiment of the present invention. The heart beat rhythms are classified after a heart beat has been classified, after the R to R interval with respect to the immediately preceding R wave has been determined, and after the heart rate corresponding to the presently analyzed heart beat and the running heart rate average have been determined.

The microprocessor begins the rhythm classification by determining in step 260 if the heart beat had been classified as a ventricular beat. If the heart beat had been classified as a ventricular beat, the microprocessor proceeds to step 262 to increment the total ventricular beat counter in the random access memory 84. Next, in step 264, the microprocessor increments the ventricular beat string counter for maintaining a total of the number of consecutive ventricular beats which have been detected. Thereafter, the microprocessor proceeds to the check timer operations to be described hereinafter.

If in step 260 the microprocessor found in the random access memory 84 that the heart beat was not a ventricular beat, it proceeds to step 266 to determine if the previous heart beat had been classified as a ventricular beat. If the previous heart beat had been a ventricular beat, the microprocessor then proceeds to step 268 to determine if the count in the ventricular beat string counter is equal to one. If the count in the ventricular string counter is not equal to one, the microprocessor proceeds to step 270 to determine if the count in the ventricular string counter is equal to two. If the ventricular string count is equal to two, the microprocessor then in step 272 records a couplet in the random access memory 84. Such a couplet is the occurrence of two consecutive ventricular beats.

If in step 270 the microprocessor determines that the ventricular beat string count is not equal to two, it then proceeds to step 274 to determine if the count in the ventricular beat string counter is equal to three. If the ventricular beat string count is equal to three, the microprocessor then in step 276 records a triplet in the random access memory 84. Such a triplet is the occurrence of three consecutive ventricular beats. If the count in the ventricular string counter is not equal to three, the microprocessor then proceeds to step 278 to determine if the count in the ventricular string counter is greater than a predetermined threshold count. If the count in the ventricular beat string counter is greater than three but less than the predetermined threshold count, the microprocessor then in step 280 records in the event counter of the random access memory 84 a non-sustained ventricular tachycardia, clears the ventricular beat string counter in step 282, and then proceeds to the check timer operations to be described hereinafter. As can thus be seen, a plurality of heart beats forms a heart rhythm and, therefore, the microprocessor stores in the random access memory 84 the classification of the previous heart beats for classifying heart beat rhythms. In addition, the implantable cardiac monitor classifies the heart beat rhythms only after detecting and classifying a heart beat as a normal sinus heart beat.

If in step 278 the microprocessor determines that the ventricular beat string count is greater than the predetermined threshold count, the microprocessor then proceeds to step 284 to record the heart beat rhythm as a ventricular tachycardia in the arrhythmia log of the random access memory 84. In recording the ventricular tachycardia in the arrhythmia log of the random access memory 84, the microprocessor time stamps the recorded ventricular tachycardia as to the date and time in which it was recorded. This enables the cardiologist, upon retrieving this data from the implanted cardiac monitor to be informed as to when the ventricular tachycardia occurred. In addition, in step 284, the microprocessor moves the ECG data corresponding to the electrocardiograms generated during the ventricular tachycardia to the ECG storage portion of the random access memory 84 to facilitate retrieval of the stored electrocardiograms by the cardiologist. In accordance with this preferred embodiment, the microprocessor stores the first and last electrocardiograms generated during the ventricular tachycardia for retrieval by the cardiologist.

After completing step 284, the microprocessor then in step 282 clears the ventricular beat string counter. It then proceeds to perform the check timer operations to be described hereinafter.

Returning now to step 268, if the microprocessor determines that the ventricular beat string count is equal to one, it then proceeds to step 288 which increments the bigeminy string counter of the random access memory 84. As well known in the art, a bigeminy rhythm is a heart beat rhythm having cycles of consecutively alternating normal sinus heart beats and ventricular beats. After incrementing the bigeminy string counter, the microprocessor then performs step 282 to clear the ventricular beat string counter. If there has been more than one such cycle of alternating normal and ventricular heart beats, the microprocessor proceeds from step 288 to step 290 to determine if there has been a bigeminy rhythm. If there has been a bigeminy rhythm, the microprocessor in step 292 records a bigeminy rhythm in the bigeminy event counter of the random access memory 84 and then increments the bigeminy string counter in accordance with step 288. Thereafter, the microprocessor clears the ventricular beat string counter in step 282 and ends.

If in step 290 it was determined that there was not a bigeminy rhythm, the microprocessor then in step 294 determines if the previous ventricular beat had been premature. In making this determination, the microprocessor retrieves the R to R interval stored in the random access memory 84 corresponding to the previous ventricular beat and compares it to a threshold which may be programmed by the cardiologist. If the previous ventricular beat was premature, the microprocessor then in step 296 records a premature ventricular contraction (PVC) in the PVC event counter. Thereafter, the microprocessor performs step 282 and ends.

If in step 294 it was determined that the previous ventricular beat was not premature, the microprocessor then proceeds to step 298 to record a ventricular ectopic beat in the ventricular ectopic beat event counter. It then proceeds to perform step 282 and ends.

Returning now to step 266, if in step 266 the microprocessor determines that the previous heart beat had not been a ventricular beat after having determined that the present heart beat is a normal sinus heart beat, the microprocessor then proceeds to step 300 to determine if there has been a bigeminy rhythm. If there has been a bigeminy rhythm, the microprocessor then proceeds to step 302 to determine whether there has been a sustained bigeminy rhythm. The microprocessor performs step 302 by determining if the bigeminy string counter contains a count which is greater than a predetermined number of counts. If the microprocessor determines in step 302 that there has been a sustained bigeminy rhythm it records and time stamps the bigeminy rhythm event in the arrhythmia log. The microprocessor also records the bigeminy string counter count in the arrhythmia log in step 304. Also in step 304 the microprocessor stores relevant data such as rhythm duration generated during the bigeminy rhythm in the arrhythmia log of the random access memory 84 for retrieval by the cardiologist. To that end, the microprocessor is responsive to the first incrementing of the bigeminy string counter for maintaining the data in the random access memory so that such data is available for transmission by the telemetry means to the cardiologist should a sustained bigeminy rhythm be determined.

Following step 304 and if in step 302 the microprocessor determines that there has not been a sustained bigeminy rhythm, the microprocessor proceeds to step 306 for clearing all bigeminy counters. Thereafter, the microprocessor ends and proceeds to the check timer operations to be described hereinafter.

If in step 300 the microprocessor determines that there has not been a bigeminy rhythm, the microprocessor then proceeds to step 308 to determine if the present normal sinus heart beat was premature. In performing step 308, the microprocessor compares the R to R interval corresponding to the present normal sinus heart beat to a predetermined threshold. If the R to R interval is less than the predetermined threshold, the microprocessor in step 310 records the present heart beat as a premature atrial contraction (PAC) in the PAC event counter of the random access memory 84. Thereafter, the microprocessor ends and enters the check timer operations.

If in step 308 the microprocessor finds that the present beat was not premature, it then proceeds to step 312 to determine if there has been a high sinus rate. In performing step 312, the microprocessor compares the determined average heart rate to a predetermined heart rate which may be programmed by the cardiologist. If the microprocessor determines in step 312 that there has not been a high sinus rate, it ends. However, if it determines in step 312 that there has been a high sinus rate, it then proceeds to step 314 to check for an irregular heart rate. Then, in step 316, it determines if there has been an irregular heart rate. If there has not, the microprocessor ends. However, if there has been an irregular heart rate, the microprocessor then proceeds to step 318 to determine if there has been a sustained irregular heart rate. If there has been a sustained irregular heart rate, the microprocessor then in step 320 records and time stamps the irregular rhythm in the arrhythmia log, saves an ECG strip in the random access memory 84, and then ends. If there has not been a sustained irregular heart rhythm, the microprocessor then in step 322 records an irregular rhythm in the irregular event counter of the random access memory 84. After each of steps 320 and 322, the microprocessor ends and proceeds to the check timer operations to be described subsequently.

Figure 14:
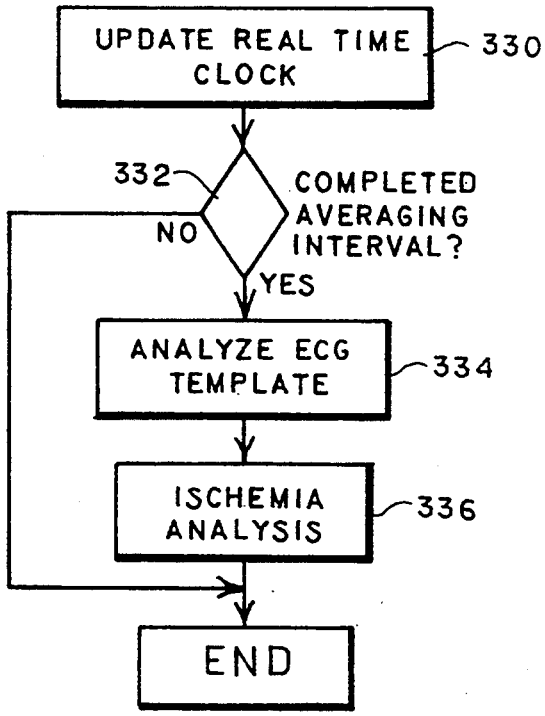
FIG. 14 is an overall flow diagram illustrating the manner in which the implantable cardiac monitor of FIG. 3 may be implemented for adapting the ECG template and performing ischemia analysis at spaced apart time intervals.

Referring now to FIG. 14, it is an overall flow diagram illustrating the manner in which the implantable cardiac monitor of FIG. 3 may be implemented for revising the ECG template and performing ischemia analysis at spaced apart time intervals. The microprocessor begins at step 330 by updating the real time clock 108 illustrated in the block diagram of FIG. 3. After updating the real time clock in step 330, the microprocessor proceeds to step 332 for determining if the spaced apart or averaging interval has been completed. As previously mentioned, this interval may be fifteen seconds. If the interval has not completed, the microprocessor ends to complete its processing of data for this heart beat and is deactivated until it receives another delayed R wave detect signal from the R wave detector 96. However, if the averaging time interval has completed, the microprocessor proceeds to step 334 to analyze the ECG template and determine ischemia analysis fiducial points as will be described subsequently with respect to FIG. 15. The microprocessor then proceeds to step 336 for performing the ischemia analysis which will be described hereinafter with respect to FIG. 16.

Figure 15:
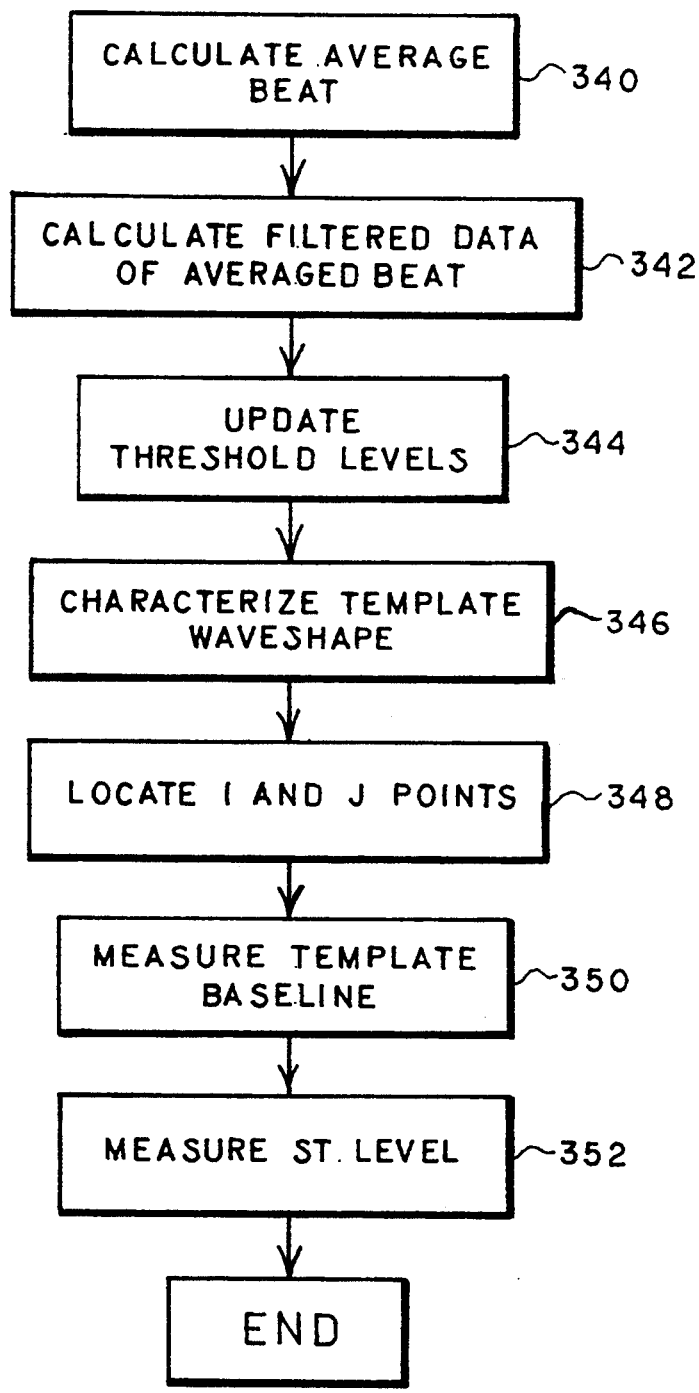
FIG. 15 is a flow diagram illustrating the manner in which the implantable cardiac monitor of FIG. 3 may be implemented for revising the ECG template at spaced apart time intervals and determining ischemia analysis fiducial points in accordance with the present invention.

Referring now to FIG. 15, it is a flow diagram illustrating the manner in which the implantable cardiac monitor of FIG. 3 may be implemented for revising the ECG template at the spaced apart time intervals and determining ischemia analysis fiducial points in accordance with this preferred embodiment of the present invention. The microprocessor begins at step 340 by calculating the average of the ECG data generated since the last template revision for those heart beats corresponding to normal sinus heart beats. Hence, the microprocessor in step 340 averages the ECG data for selected ones of the electrocardiograms generated responsive to the heart beats which occurred since the last template revision. In step 342 the microprocessor calculates filtered data of the averaged heart beat calculated in 340 and then in step 344 updates the threshold levels of the averaged heart beat. Then, in step 346, the microprocessor determines the new template wave shape and sets the new maximum and minimum levels for the revised template. In performing step 346, the microprocessor relies upon the previous template and revises the previous template in accordance with the weighted average of the averaged heart beat calculated in step 340.

After the revised template has been determined, the microprocessor locates the i and j fiducial points of the ECG corresponding to the present heart beat in step 348. Such i and j points have been previously shown and described with respect to FIG. 6. Next, in step 350, the microprocessor measures the template baseline, that is, the level of the i point of the revised template. Then, in step 352, the microprocessor determines the deviation in the ST level between the template baseline and the level at some predetermined point, for example, 80 milliseconds after the j point, to determine ST level deviation at the ST point. Thereafter, the microprocessor ends and enters the ischemia analysis illustrated in FIG. 16.

Figure 16:
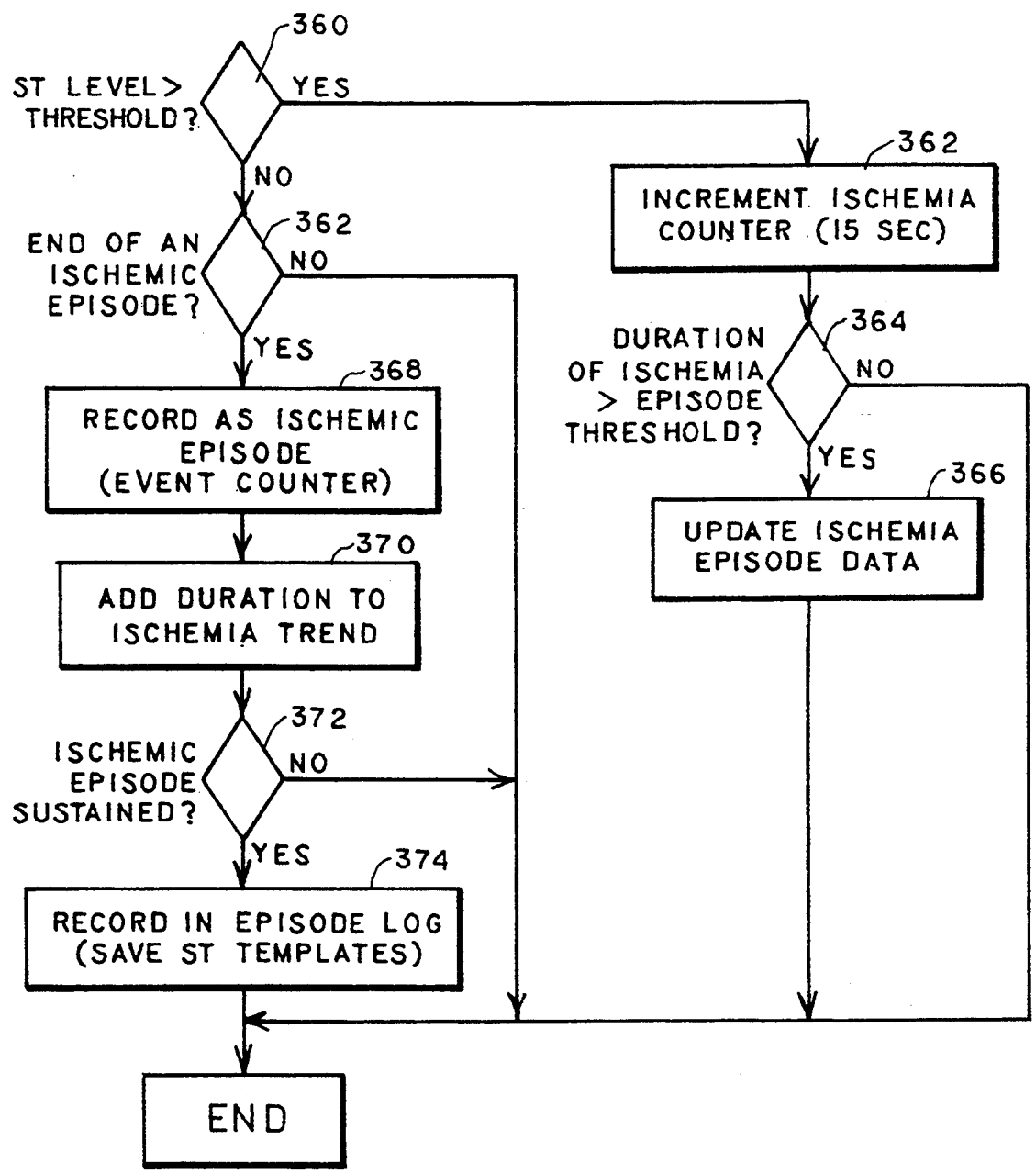
FIG. 16 is a flow diagram illustrating the manner in which the implantable cardiac monitor of FIG. 3 may be implemented for performing ischemia analysis in accordance with the present invention.

Referring now to FIG. 16, it is a flow diagram illustrating the manner in which the implantable cardiac monitor of FIG. 3 may be implemented for performing ischemia analysis in accordance with this preferred embodiment of the present invention.

The microprocessor begins at step 360 to determine if the magnitude of the ST level deviation is greater than a threshold level of either ST elevation or ST depression. Such a threshold level is preferably programmable by the cardiologist. If the ST level deviation is greater than the threshold, the microprocessor proceeds to step 362 to increment the ischemia counter of the random access memory 84. The microprocessor then, in step 364, determines if the duration of the ischemia is greater than an episode threshold. If it is not, the microprocessor ends. If however the duration of the ischemia is greater than an episode threshold, the microprocessor then in step 366 updates the ischemia episode data in the random access memory 84. Such data may include the current duration of the ischemic episode. The microprocessor then ends.

In step 360 if the microprocessor finds that the ST level deviation is less than the threshold, the microprocessor then proceeds to step 362 to determine if this is an end of an ischemic episode. In performing step 362, the microprocessor determines if ischemia data has been retained in the random access memory. If the microprocessor fails to detect ischemia data retained in the random access memory, it will then end. However, if the microprocessor finds ischemia data in the random access memory in performing step 362, it proceeds to step 368 to record an ischemic episode in the ischemia event counter of the random access memory 84. Hence, as can be seen, the implantable cardiac monitor characterizes ischemia episodes after there has been detected ischemia immediately followed by the determination of an ST level deviation which is less than the threshold limit.

After step 368, the microprocessor proceeds to step 370 to add the duration of this last detected ischemic episode to the ischemia trend data stored in the random access memory 84. Next, in step 372, the microprocessor determines if the ischemic episode was a sustained episode. If it was not sustained, the microprocessor ends. If the ischemic episode was sustained, that is, if the ischemia episode duration was greater than a predetermined time, the microprocessor then proceeds to step 374 to record the ischemic episode in the ischemic episode log of the random access memory 84. Also, at this time, the microprocessor transfers the ECG data generated during the sustained ischemia episode to the ECG strip store of the random access memory 84 for retrieval by the cardiologist through the telemetry. Such ischemia data is maintained within the random access memory by the microprocessor upon the detecting of an onset of ischemia in accordance with step 360. Also, when the sustained ischemic episode is recorded in the log, the sustained ischemic episode is also time stamped by the microprocessor.

Figure 17:
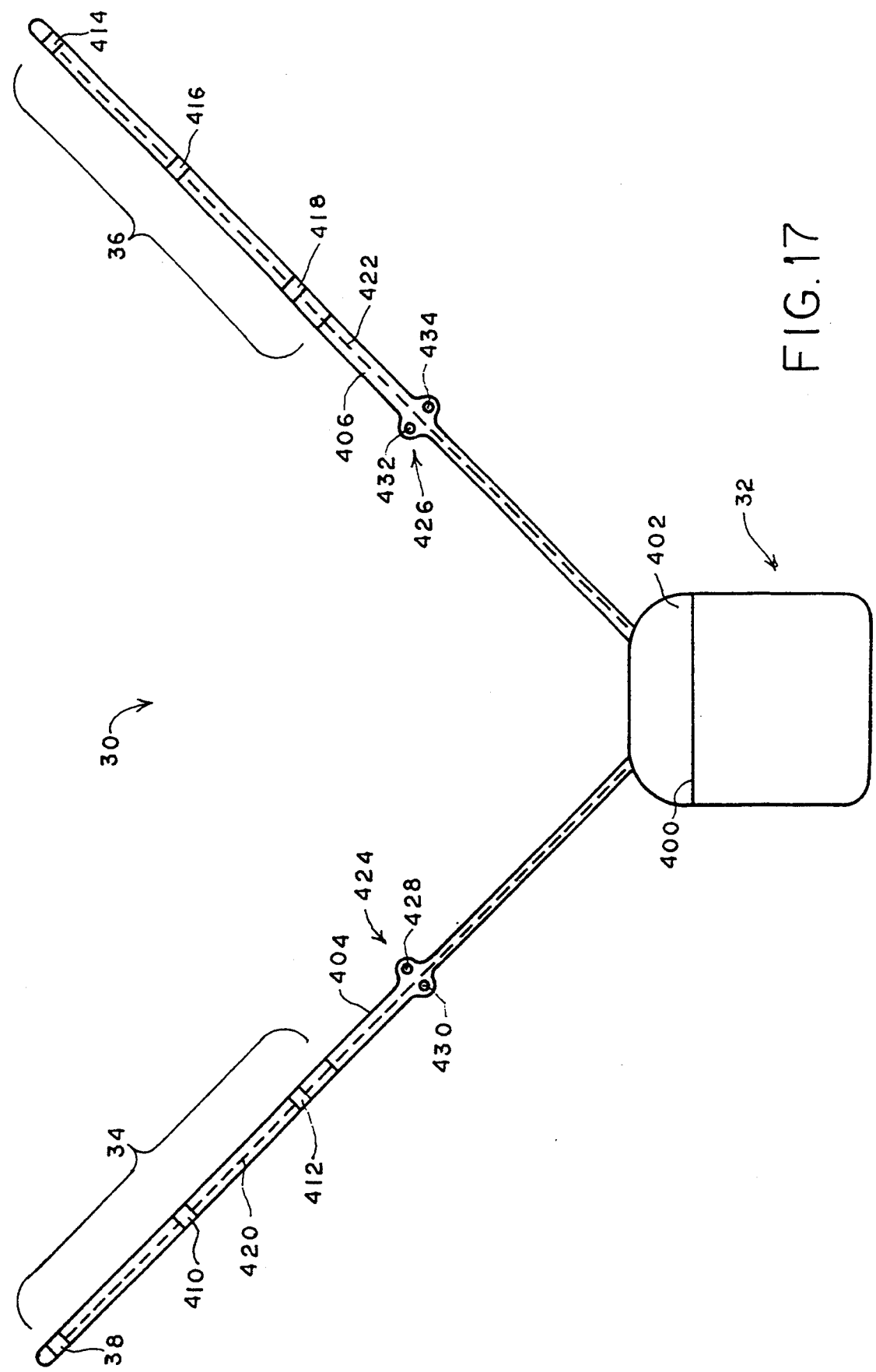
FIG. 17 is a front plan view of an implantable cardiac monitor including an electrode system employing catheter electrodes for sensing heart activity and configured in accordance with one preferred embodiment of the present invention.

Referring now to FIG. 17, it is a front plan view of an implantable cardiac monitor 30 including an electrode system employing catheter electrodes for sensing heart activity and configured in accordance with one preferred embodiment of the present invention. The implantable cardiac monitor 30 includes an enclosure 32 for containing electrical circuitry, preferably as previously described herein, for monitoring the physiology of the human heart. The enclosure includes an upper perimeter 400. The electrode system includes an electrically insulating header 402 sealingly engaged with the upper perimeter 400 of the enclosure 32, first and second flexible insulative conduits 404 and 406 respectively extending from the header 402, and first and second electrode means 34 and 36 carried by each of the first and second conduits 404 and 406 respectively. The first and second electrode means 34 and 36 each include three spaced apart electrically conductive electrodes with the first electrode means including electrodes 408, 410, and 412, and the second electrode means 36 including electrodes 414, 416, and 418. Conductor means 420 extends through the first conduit 404 and into the header 402 for coupling each of the electrodes 408, 410, and 412 individually to the electrical circuitry within the enclosure 32. Similarly, conductor means 422 extends through the second conduit 406 and into the header 402 for individually coupling the electrodes 414, 416, and 418 to the electrical circuitry within enclosure 32.

In accordance with this preferred embodiment, each of the electrodes 408, 410, 412, 414, 416, and 418 is ring-shaped and has an outer diameter which is substantially equal to the outer diameter of the flexible insulative conduits 404 and 406. As a result, when the cardiac monitor 30 is implanted beneath the skin of a patient, each of the electrodes will make electrical contact with the heart for detecting heart activity. Preferably, the electrodes upon implantation are placed beneath the skin of a patient to dispose the electrodes in nontouching proximity to the heart for establishing the electrical contact between the electrodes and the heart. Also, it will be noted that the first and second conduits 404 and 406 extend from the header 402 in a substantially V-shaped configuration so that, when the enclosure 32 is implanted as illustrated in FIG. 1, the electrodes will be in close proximity to the $V_2$ to $V_6$ precordial locations as illustrated in FIG. 1.

Each of the first and second conduits 404 and 406 also include a suture means 424 and 426 respectively which are integrally formed in the flexible conduits and include a pair of holes 428 and 430 in suture means 424 and 432 and 434 in suture 426. With this configuration, the suture means permit the first and second conduits 404 and 406 to be sutured in place for providing fixation for the electrodes of the first and second electrode means 34 and 36.

Figure 18:
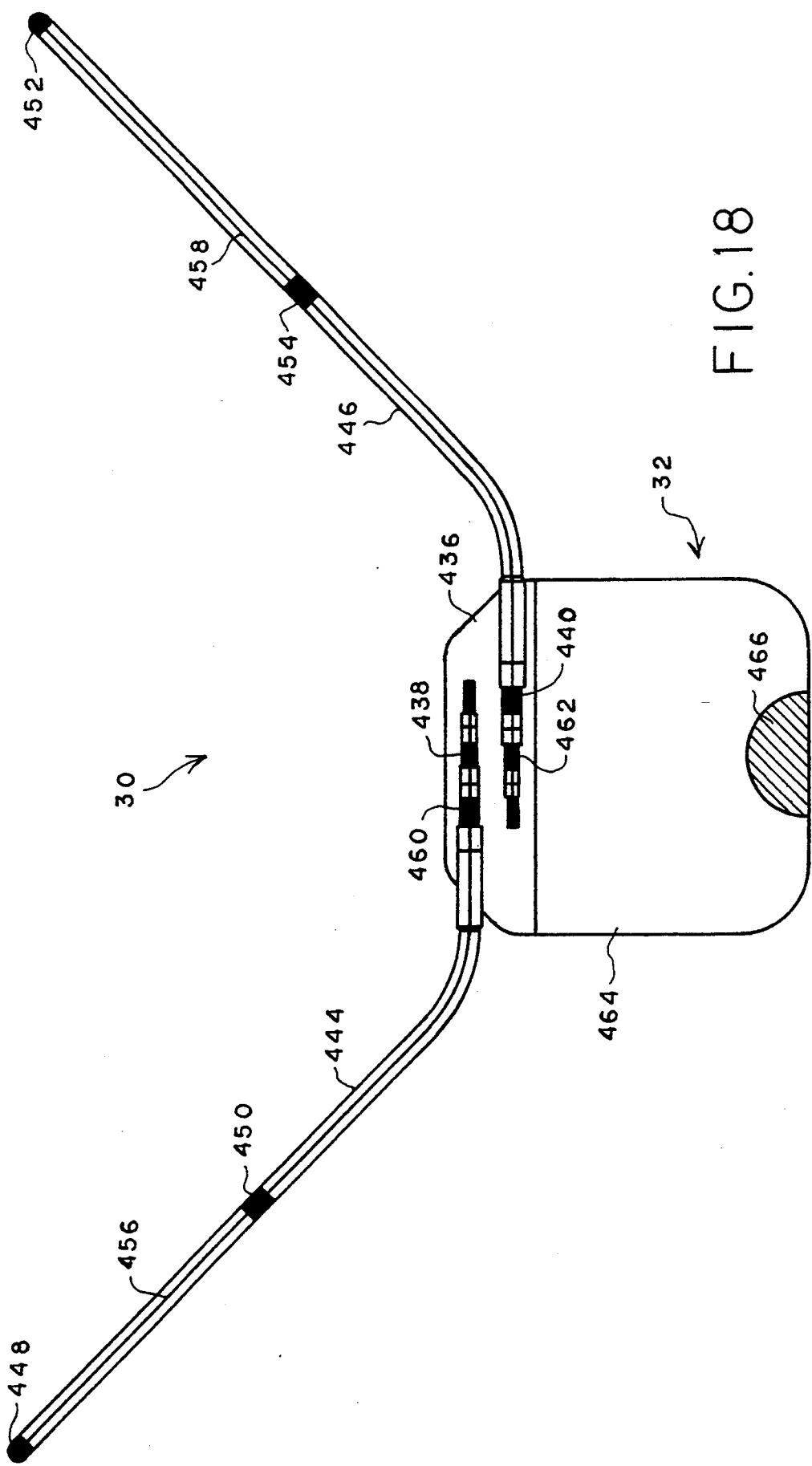
FIG. 18 is a front plan view of an implantable cardiac monitor including another electrode system employing catheter electrodes for sensing heart activity and configured in accordance with another preferred embodiment of the present invention.

Referring now to FIG. 18, it is a front plan view of another implantable cardiac monitor 30 employing catheter electrodes for sensing heart activity and is configured in accordance with another preferred embodiment of the present invention. Again, the cardiac monitor includes an enclosure 32, an insulative header 436 which includes a first connector receptacle 438 and a second connector receptacle 440.

First and second insulative conduits 444 and 446 each carry a pair of spaced apart ring-shaped catheter electrodes with conduit 444 carrying electrodes 448 and 450 and conduit 446 carrying electrodes 452 and 454. Conductor means 456 extends through conduit 444 to individually electrically couple electrodes 448 and 450 to the contacts of an electrical connector 460. Similarly, conductor means 458 extends through conduit 446 for individually electrically connecting electrodes 452 and 454 to the contacts of a second connector 462. This permits the electrodes 448, 450, 452, and 454 to be electrically coupled to the electrical circuitry within enclosure 32.

The enclosure 32 includes a surface portion 464 which includes an electrically conductive portion 466. Upon implantation of the cardiac monitor 30, the conductive portion 466 provides a ground reference for the sensing of heart activity by the electrodes 448, 450, 452, and 454. Also, it will be noted in the figure, that the conduits 444 and 446 are resiliently preformed so as to extend from the header 436 in a substantially V-shaped configuration for reasons previously described.

In forming the electrically conductive portion 466 on surface 464 of enclosure 32, the enclosure 32 may be formed of insulative material and the conductive portion 466 formed by a coating of electrically conductive material. Alternatively, the enclosure may be formed from electrically conductive material which is covered by an insulative coating except for the portion 466 to expose the conductive portion 466 beneath insulative coating.

Figure 19:
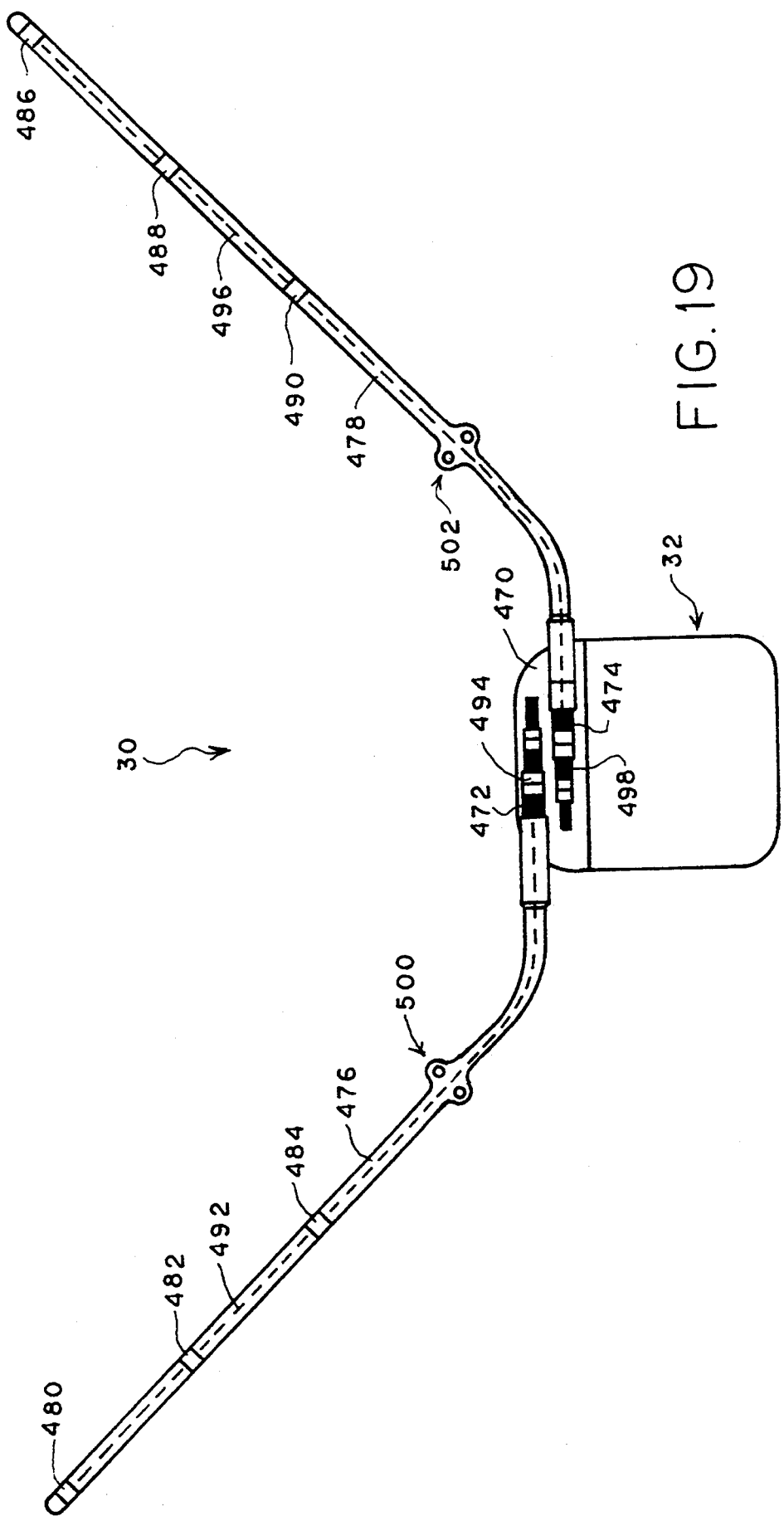
FIG. 19 is a front plan view of an implantable cardiac monitor including a further electrode system employing catheter electrodes for sensing heart activity and configured in accordance with a further preferred embodiment of the present invention.

Referring now to FIG. 19, it illustrates another preferred embodiment of a cardiac monitor 30 embodying the present invention. The embodiment of FIG. 19 is similar to the embodiment of FIG. 18 in that the enclosure 32 includes an insulative header 470 which includes first and second connector receptacles 472 and 474. The flexible conduits 476 and 478 each carry three spaced apart ring-shaped catheter electrodes with conduit 476 carrying electrodes 480, 482, and 484, and conduit 478 carrying electrodes 486, 488, and 490. First conductor means 492 electrically couples the electrodes 480, 482, and 484 to the contacts of a first connector 494 which is arranged to mate with the connector receptacle 472. Similarly, second conductor means 496 electrically couples the electrodes 486, 488, and 490 to contacts of a second connector 498 which is arranged to mate with the connector receptacle 474. As a result, with the contacts of the receptacles 472 and 474 being coupled to the electrical circuitry contained within the enclosure 32, the electrodes are coupled to the electrical circuitry.

As in the embodiment of FIG. 18, the conduits 476 and 478 are resiliently preformed so that they extend in a substantial V-shaped configuration from the header 470. Like the embodiment of FIG. 17, the conduits 476 and 478 each include suture means 500 and 502 integrally formed therein for fixing the electrodes in place upon implantation of the cardiac monitor 30. As may also be noted in FIGS. 18 and 19, the connector receptacles 460 and 462 and 472 and 474 are disposed in opposing relation. This permits the conduits to directly extend from the headers in opposed relation.

Figure 20:
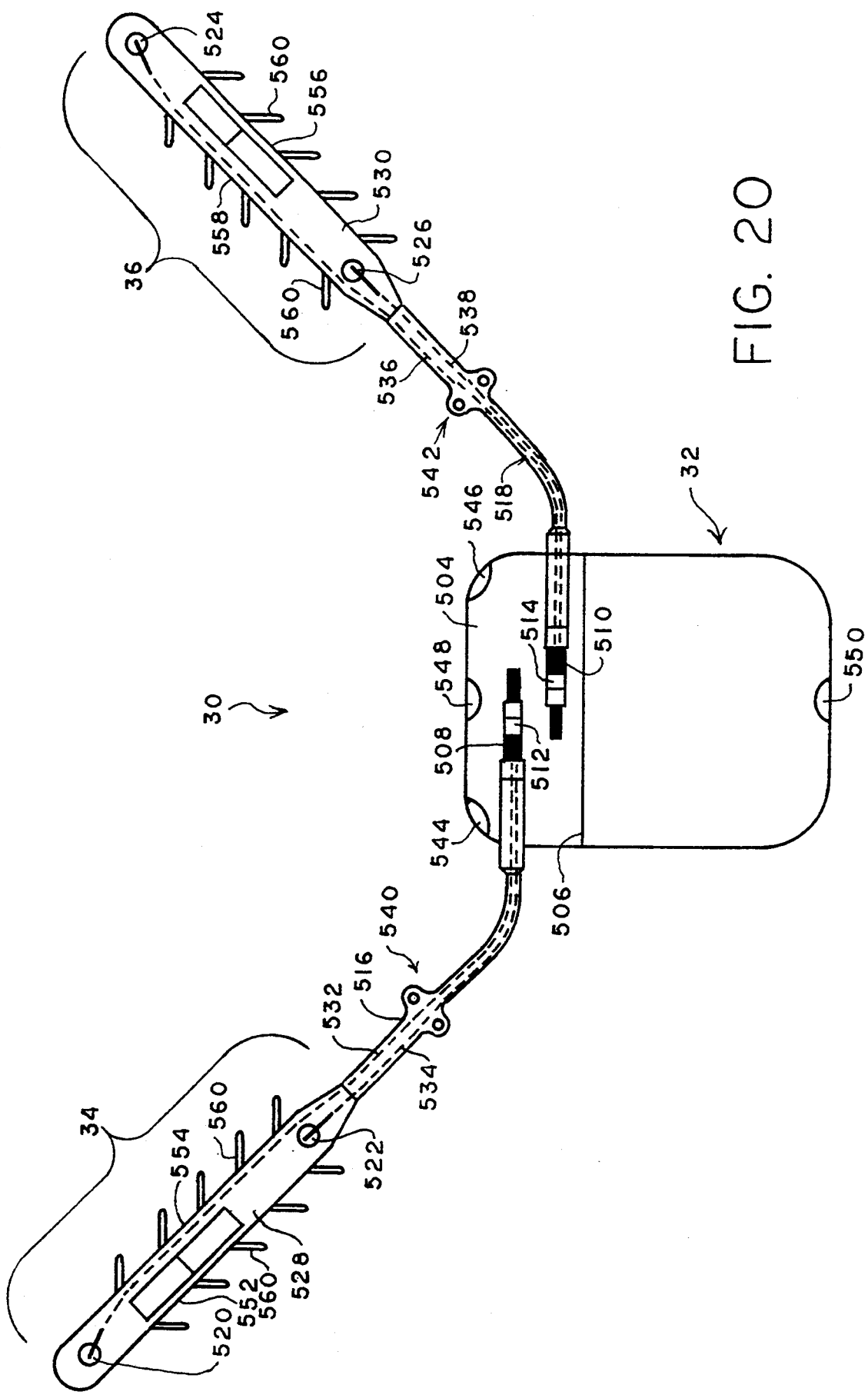
FIG. 20 is a front plan view of an implantable cardiac monitor including an electrode system employing strip electrodes for sensing heart activity and configured in accordance with another preferred embodiment of the present invention.

Referring now to FIG. 20, it illustrates another implantable cardiac monitor 30 embodying further aspects of the present invention. As will be seen hereinafter, the cardiac monitor 30 may be utilized in a leadless configuration wherein the electrical conduits and electrodes carried thereby are not utilized or a configuration where the conduits and electrodes carried on the conduits are utilized. The cardiac monitor illustrated in FIG. 20, as in the previous embodiments of FIGS. 17-19 includes an enclosure 32 for enclosing the electrical circuitry of the cardiac monitor. An insulative header 504 sealingly engages an upper perimeter 506 of the enclosure 32. The header includes a first connector receptacle 508 and a second connector receptacle 510 disposed in opposed relation. The receptacles 508 and 510 are arranged for matingly receiving first and second connectors 512 and 514 respectively. The connectors 508 and 510 are coupled to conduits 516 and 518 respectively. Each of the conduits 516 and 518 carry an electrode means 34 and 36 respectively. The electrode means 34 and 36 comprise strip electrodes which include discrete, pill-shaped, conductive electrodes with electrode means 34 including a pair of electrodes 520 and 522 and electrode means 36 including electrodes 524 and 526. The strip electrode means 34 and 36 each include an elongated strip of flexible material 528 and 530 respectively with the discrete electrodes 520 and 522 and 524 and 526 embedded therein but having an exposed major surface for establishing electrical contact with the heart for sensing heart activity. Conductors 532 and 534 extend through the flexible strip 528 and conduit 516 for coupling electrodes 520 and 522 to the contacts of connector 512. Similarly, conductors 536 and 538 extend through flexible strip 530 and conduit 518 for electrically coupling electrodes 524 and 526 to the contacts of connector 514. With the connectors being received by the receptacles, and the contacts of the receptacles being coupled to the electrical circuitry within enclosure 32, the electrodes are coupled to the electrical circuitry to enable the cardiac monitor to monitor the physiology of the heart.

As will also be noted, the conduits 516 and 518 each include a suture means 540 and 542 of the type previously described. As a result, when the cardiac monitor 30 is implanted, the suture means 540 and 542 permit the electrodes to be fixed in place.

In addition to the foregoing, the header 504 also includes conductive portions 544, 546, and 548. Also, the enclosure 32 includes a conductive portion 550. When the cardiac monitor 30 is to be utilized for detecting and analyzing arrhythmias, it may be unnecessary to utilize the electrode means 34 and 36. Instead, the conductive portions 544 and 546 may be utilized for monitoring heart activity with conductive portion 550 serving as a ground reference for such sensing. Conductive portion 548 may also be utilized for sensing or, alternatively, may be utilized for providing a low energy subcutaneous stimulus to the patient for the purpose of providing alarms to the patient as previously described.

In addition to the suture means 540 and 542 provided on conduits 516 and 518, for fixing the electrode means 34 and 36 in place upon implantation, it will be noted that the elongated strips 528 and 530 each include a pair of longitudinal side walls 552 and 554 and 556 and 558. Extending from the longitudinal side walls 552, 554, 556, and 558 are fixation projections 560. The projections 560 form acute angles with the longitudinal side walls 552, 554, 556, and 560. Upon implantation of the cardiac monitor 30, tissue will grow around the fixation projections 560 for fixing the electrode means 34 and 36 in place to assure stability of the implantable cardiac monitoring system.

Figure 21:
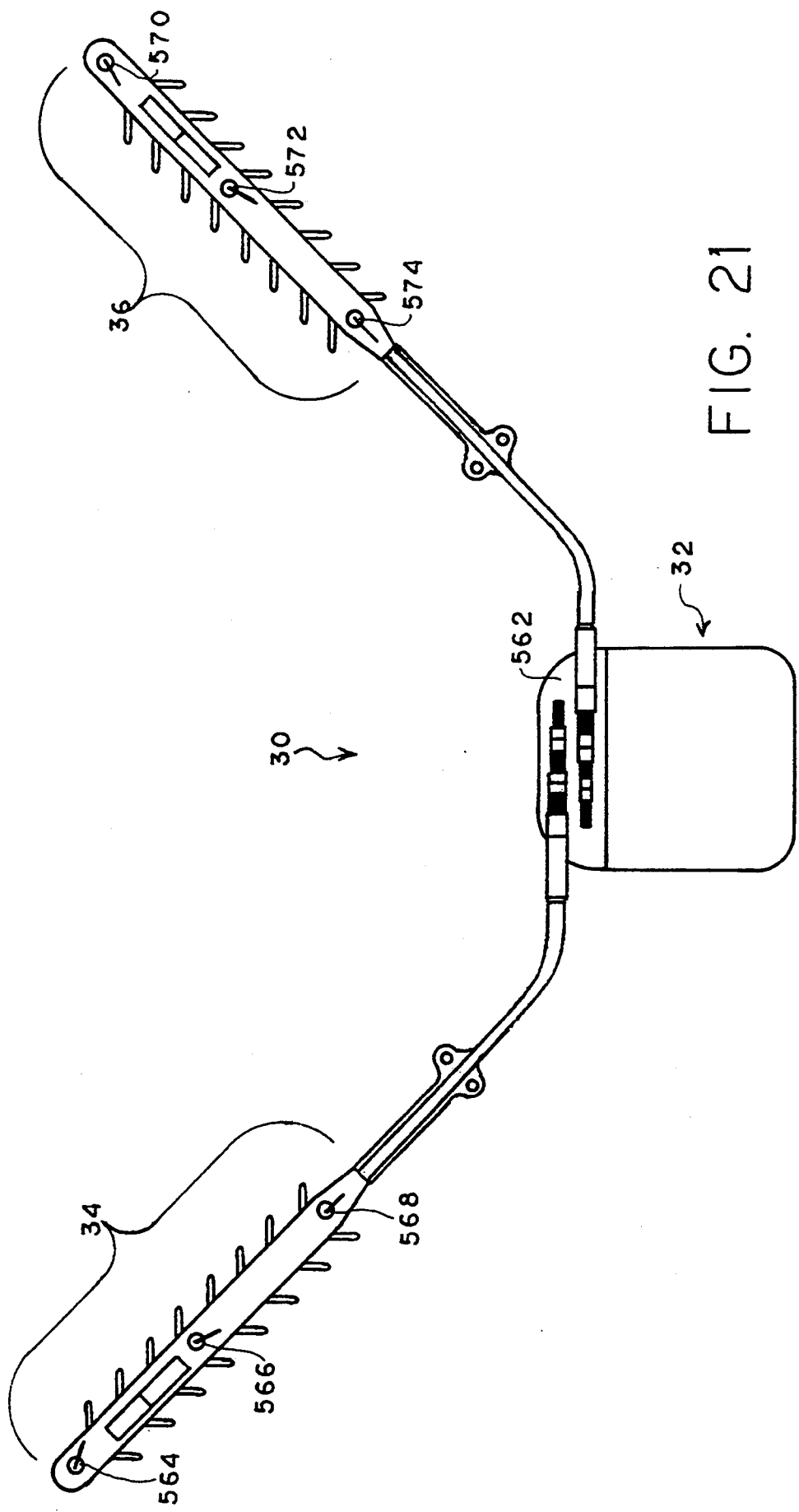
FIG. 21 is a front plan view of an implantable cardiac monitor including a further electrode system employing strip electrodes for sensing heart activity and configured in accordance with a further preferred embodiment of the present invention.

Referring now to FIG. 21, it illustrates another implantable cardiac monitor 30 embodying the present invention. The cardiac monitor illustrated in FIG. 21 is similar to the cardiac monitor illustrated in FIG. 20 and therefore the similarities need not be described in detail herein. However, it is to be noted that the enclosure 32 and the header 562 of the implantable cardiac monitor 30 do not include the conductive surface portions as illustrated in FIG. 20. In addition, the electrode means 34 and 36 each include three discrete, pill-shaped, conductive electrodes with electrode means 34 including electrodes 564, 566, and 568, and electrode means 36 including electrodes 570, 572, and 574.

Figure 22:
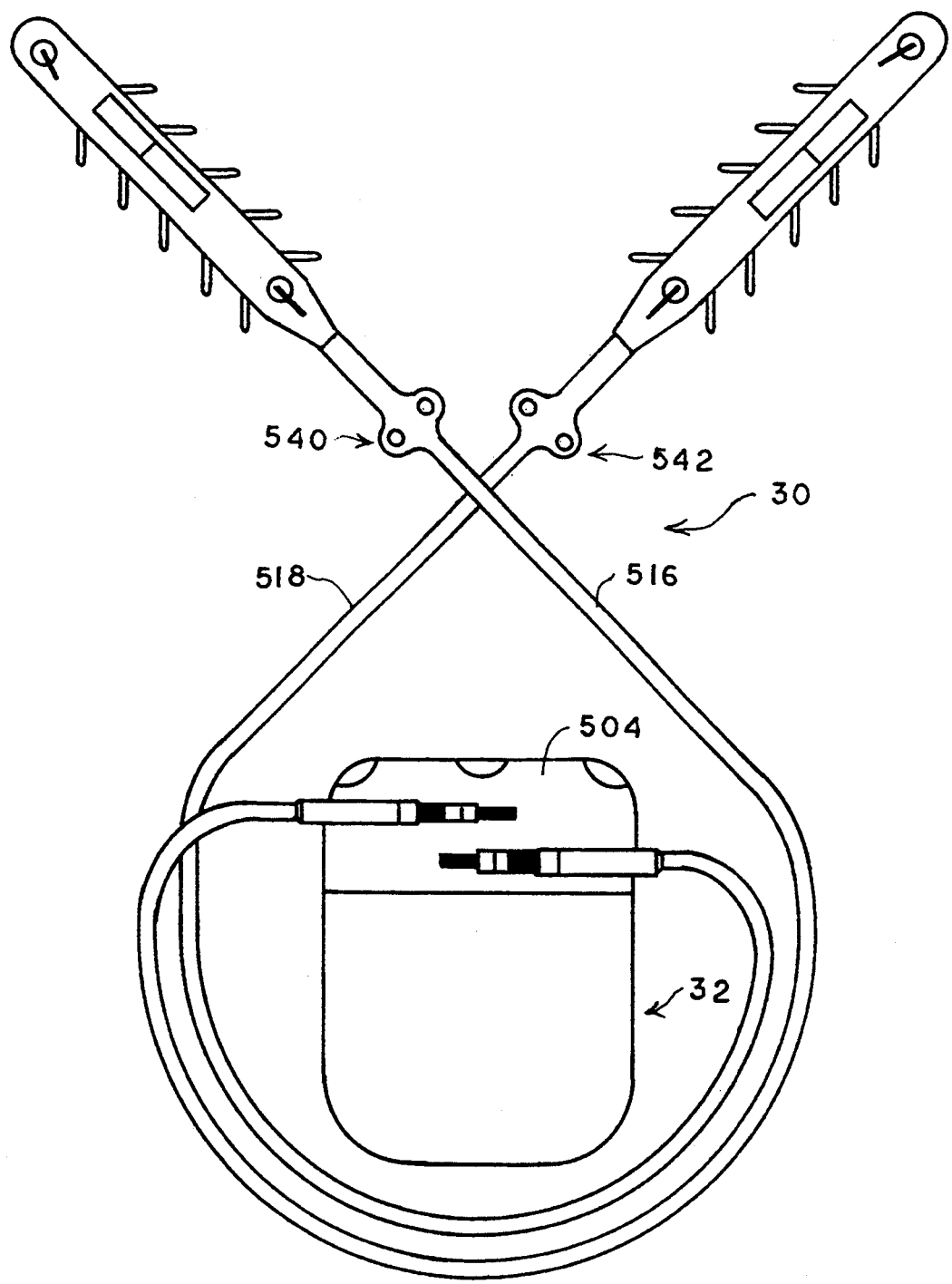
FIG. 22 is a front plant view of an implantable cardiac monitor including a further electrode system employing strip electrodes for sensing heart activity and configured in accordance with a still further preferred embodiment of the present invention to provide strain relief for the strip electrodes.

Referring now to FIG. 22, it illustrates another implantable cardiac monitor 30 embodying the present invention. The cardiac monitor 30 of FIG. 22 is essentially identical to the cardiac monitor illustrated in FIG. 20 except that the conduits 516 and 518 are of a length to enable the conduit means to be looped around the enclosure 32 to provide strain relief for the conduit means 516 and 518 between the suture means 540 and 542 and the header 504. This gives the cardiologist a greater degree of flexibility in locating the position of the enclosure 32 upon implantation of the implantable cardiac monitor of FIG. 22.

Figure 23:
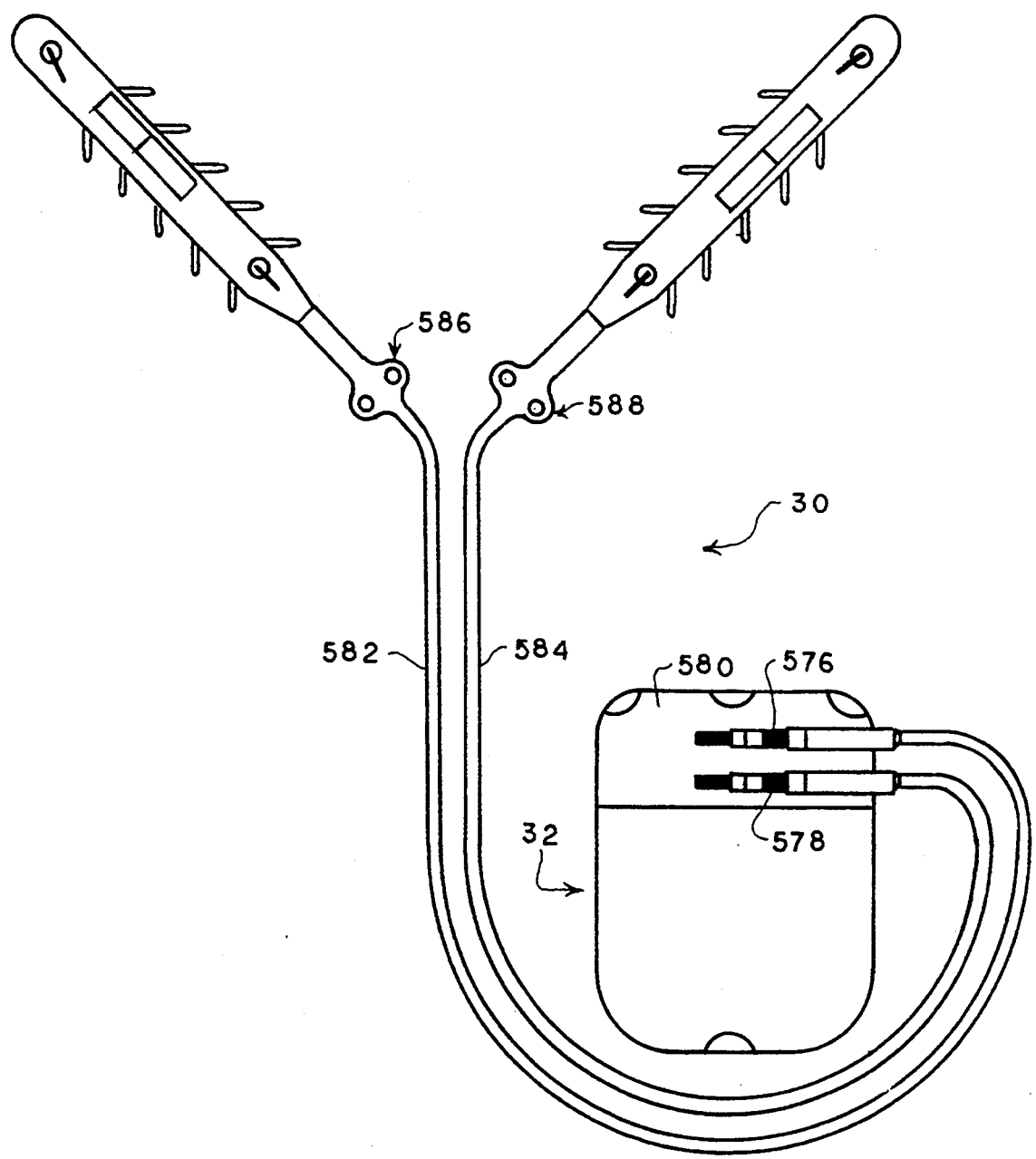
FIG. 23 is a front plan view of an implantable cardiac monitor including a still further electrode system employing strip electrodes for sensing heart activity and configured in accordance with a still further preferred embodiment of the present invention for providing strain relief for the strip electrodes.

Referring now to FIG. 23, it illustrates another implantable cardiac monitor 30 which is similar to the implantable cardiac monitor of FIG. 22. Here, it will be seen, that the connector receptacles 576 and 578 are arranged within the header 580 in non-opposing relation. Like the previous embodiment however, the conduits 582 and 584 are of sufficient length to enable the conduit means 582 and 586 to be looped around the enclosure 32 to provide strain relief for the conduits 582 and 584 between the suture means 586 and 588.

Figure 25:
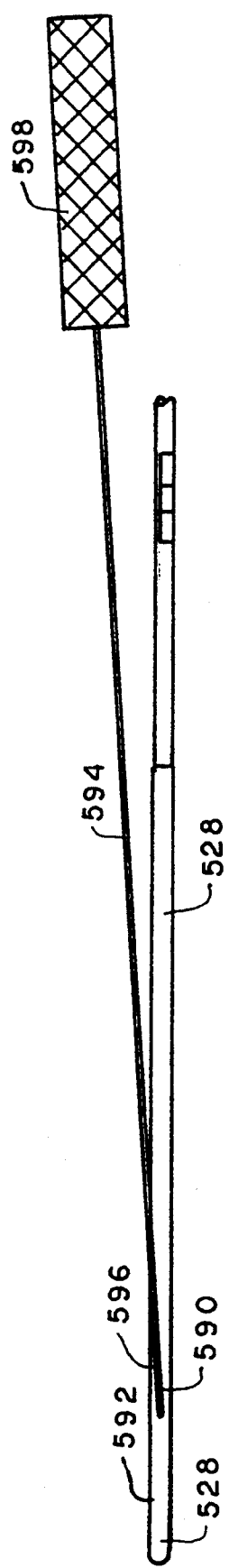
FIG. 25 is a side plan view of the strip electrode of FIG. 24.
Figure 24:
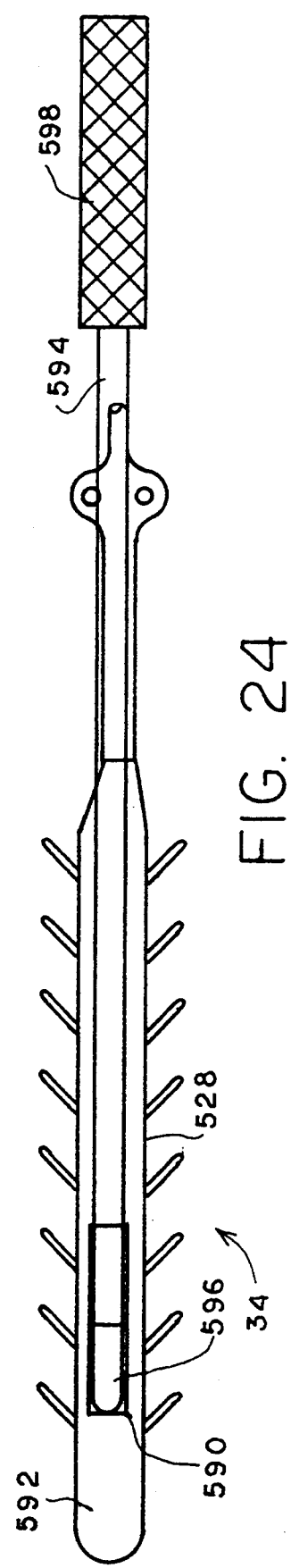
FIG. 24 is a top plan view of one of the strip electrodes in conjunction with a positioning tool which may be utilized in accordance with the present invention for positioning the strip electrode during the implantation thereof.

Referring now to FIG. 24, it is a top plan view of one of the strip electrodes in conjunction with a positioning tool which may be utilized in accordance with the present invention for positioning the strip electrode during the implantation thereof. FIG. 25 is a side plan view of the strip electrode of FIG. 24. For purposes of this discussion, it will be assumed that the strip electrode illustrated in FIGS. 24 and 25 is strip electrode 34 of FIG. 20. As can be seen in FIGS. 24 and 25, the elongated strip of flexible material 528 includes a slot 590 within the top surface 592. An elongated tool 594 has a distal end 596 configured to be received within the slot 590. This facilitates the movement of the strip electrode 34 into a desired position upon implantation of the strip electrode beneath the skin of a patient. To facilitate such positioning, the tool 594 includes a handle 598 at the proximal end thereof which may be gripped by the cardiologist.

Figure 26:
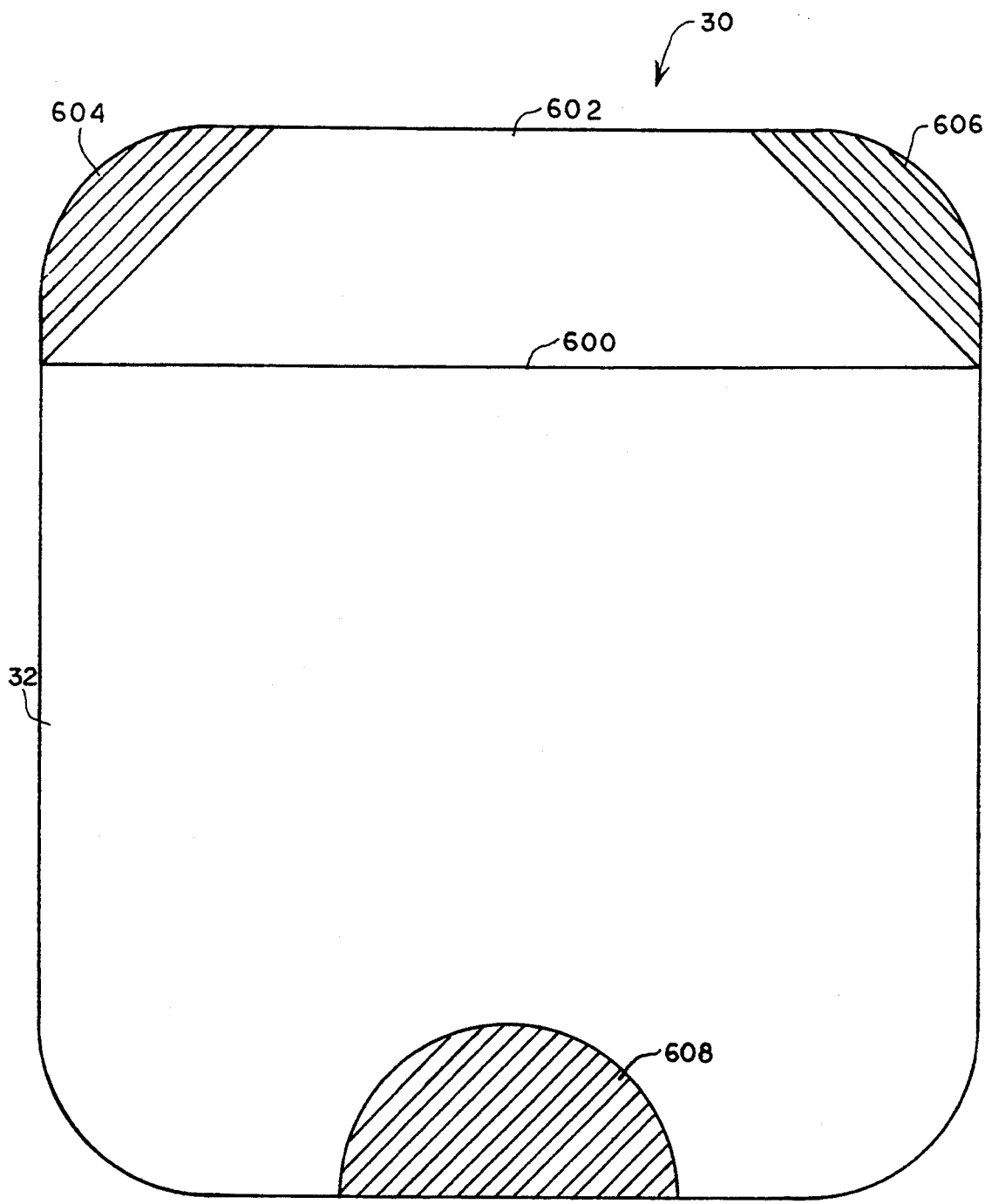
FIG. 26 is a front plan view of an implantable cardiac monitor embodying the present invention which employs a leadless electrode system in accordance with a further embodiment of the present invention.

Referring now to FIG. 26, it is a front plan view of another implantable cardiac monitor 30 embodying the present invention which employs a leadless electrode system. The cardiac monitor 30 of FIG. 26 includes a hermetically sealed enclosure 32 defining a cavity having an opened perimeter 600 and a header 602 sealingly engaging the perimeter 600. The cardiac monitor 30 further includes first and second electrical conductors 604 and 606 respectively which cover first and second respective discrete portions of the enclosure for forming first and second sensing electrodes respectively for sensing activity of the heart. In accordance with this preferred embodiment, the first and second electrical conductors cover respective portions of the header 602.

The cardiac monitor 30 further includes a third electrical conductor 608 covering a third discrete portion of the enclosure for forming a reference electrode. The circuit means utilized within the enclosure 32 may be the electrical circuitry previously described in accordance with the preferred embodiment of the present invention.

It will be noted that the first and second electrical conductors 604 and 606 are equally spaced from the third electrical conductor 608. This ensures symmetrical sensing of heart activity at the electrodes 604 and 606. In forming the electrodes 604 and 606, the header may be formed from electrically insulating material with the first and second electrical conductors being an electrically conductive coding covering the respective discrete portion of the header.

Figure 27:
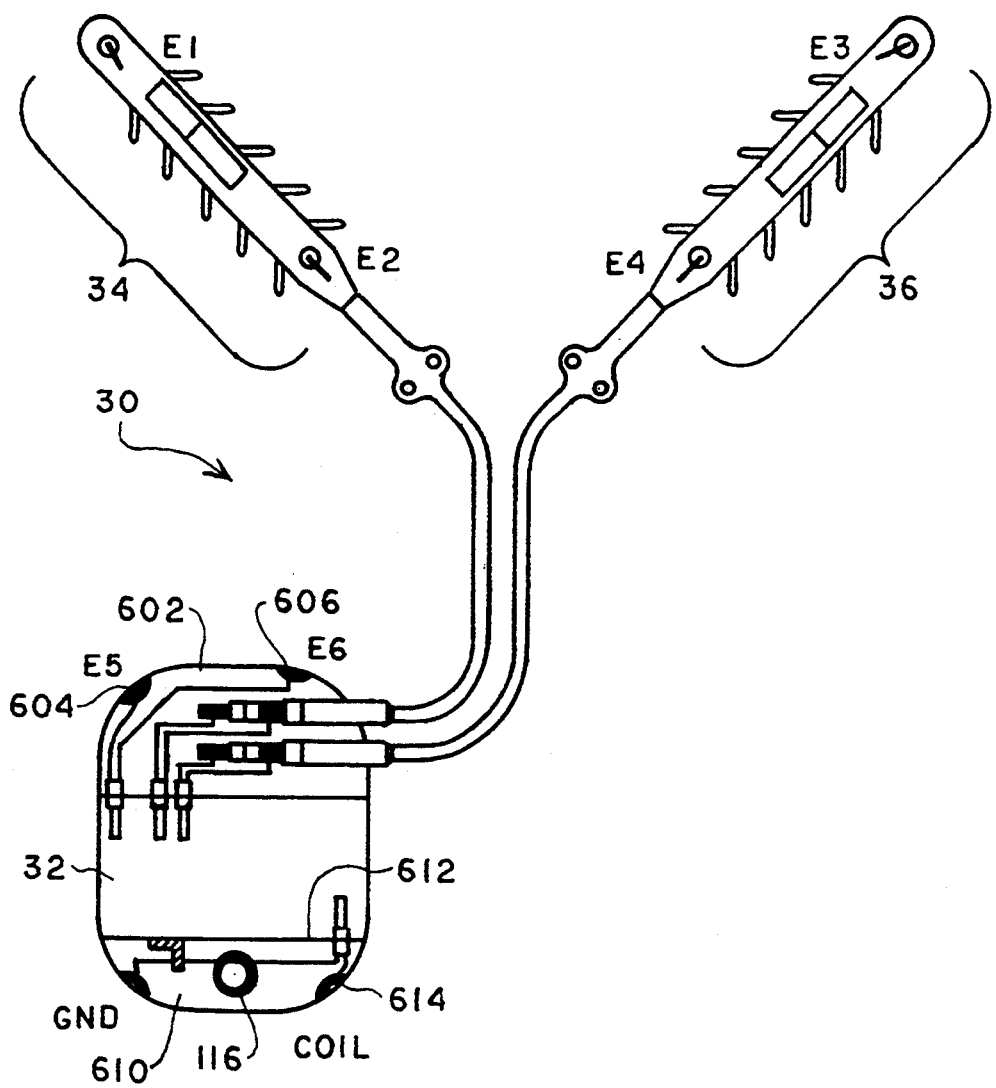
FIG. 27 is a front plan view of an implantable cardiac monitor illustrating a preferred location for telemetry means for efficiently transmitting data characterizing the physiology of the heart from the implantable cardiac monitor to an external receiver.

Referring now to FIG. 27, it illustrates a still further implantable cardiac monitor 30 embodying the present invention. The cardiac monitor 30 of FIG. 27 is similar to the cardiac monitor 30 of FIG. 26 except that in addition to electrodes 604 and 606, it additionally provides for electrode means 34 and 36 of the type previously described. However, as will be noted in FIG. 27, the cardiac monitor 30 there illustrated also includes a second header 610 in addition to the header 602. The enclosure 32 includes an additional perimeter 612 with the additional header 610 sealingly engaging the additional perimeter 612. Within the additional or second header 612 is the telemetry means coil antenna 116 as illustrated in FIG. 3. Because the telemetry means is located within the insulative header 610, efficient telemetry of data to be retrieved by the cardiologist will be provided. In accordance with this preferred embodiment, the enclosure 32 may enclose the electrical circuitry previously described.

In addition to the foregoing, the cardiac monitor of FIG. 27 includes a further discrete electrode 614. This further electrode 614 may be utilized for providing the aforementioned low energy subcutaneous stimulations to the patient for purposes of providing the patient with the alarms as previously described.

While particular embodiments of the present invention has been shown and described, modifications may be made, and it is therefore intended in the appended claims to cover all such changes and modifications which fall within the true spirit and scope of the invention.

What is claimed is:

1. An electrode system for use with a fully implantable cardiac monitor of the type including electrical circuitry for monitoring the physiology of the human heart and having an enclosure for containing said electrical circuitry, said electrode system comprising:

first and second flexible insulative conduits;

first and second electrode means carried by each of said first and second conduits respectively, said first and second electrode means comprising strip electrode means including an elongated strip of flexible material including a plurality of spaced apart discrete conductive electrodes embedded therein, said electrodes having an exposed major surface, each said elongated strip of flexible material including opposing longitudinal walls and a plurality of spaced apart fixation projections projecting from said longitudinal walls, said fixation projections forming acute angles with said longitudinal walls;

conductor means extending through said first and second conduits and into said header for coupling said electrodes of said first and second electrode means to said electrical circuitry, said conduits and said electrode means being implantable beneath the skin of a patient to dispose said electrodes in non-touching proximity to the heart for establishing electrical contact between said electrodes and the heart.

* * * * *

UNITED STATES PATENT AND TRADEMARK OFFICE
CERTIFICATE OF CORRECTION

PATENT NO. : 5,388,578

DATED : February 14, 1995

INVENTOR(S) : Yomtov et al.

It is certified that error appears in the above-identified patent and that said Letters Patent is hereby corrected as shown below:

| Column | Line | | |
|--------|------|---|---|
| 6 | 36 | "plant" should be | --plan-- |
| 8 | 18 | "beat," should be | --beat.-- |
| 9 | 48 | "80" should be | --88-- |
| 30 | 60 | "header" should be | --enclosure-- |

Signed and Sealed this

Sixteenth Day of May, 1995

Attest:

BRUCE LEHMAN

*Attesting Officer*       *Commissioner of Patents and Trademarks*